US009636523B2

United States Patent
Smith et al.

(10) Patent No.: US 9,636,523 B2
(45) Date of Patent: May 2, 2017

(54) BRACHYTHERAPY DOSE VERIFICATION APPARATUS, SYSTEM AND METHOD

(76) Inventors: Ryan Lee Smith, Montrose (AU); Rick Don Franich, South Morang (AU)

(*) Notice: Subject to any disclaimer, the term of this patent is extended or adjusted under 35 U.S.C. 154(b) by 10 days.

(21) Appl. No.: 13/822,278

(22) PCT Filed: Sep. 13, 2010

(86) PCT No.: PCT/AU2010/001188
§ 371 (c)(1),
(2), (4) Date: May 9, 2013

(87) PCT Pub. No.: WO2012/034157
PCT Pub. Date: Mar. 22, 2012

(65) Prior Publication Data
US 2013/0303902 A1    Nov. 14, 2013

(51) Int. Cl.
*A61N 5/10* (2006.01)
*A61B 6/12* (2006.01)

(52) U.S. Cl.
CPC .............. *A61N 5/1071* (2013.01); *A61B 6/12* (2013.01); *A61N 5/1001* (2013.01);
(Continued)

(58) Field of Classification Search
CPC .................................................... A61N 5/1071
(Continued)

(56) References Cited

U.S. PATENT DOCUMENTS 5,405,309 A * 4/1995 Carden, Jr. ...................... 600/3
5,635,709 A    6/1997 Sliski et al.
(Continued)

FOREIGN PATENT DOCUMENTS

AU    2008100728         10/2008
AU    2008100728 A4 *    10/2008    ............ A61M 36/12
(Continued)

OTHER PUBLICATIONS

Khoo Radiotherapeutic Techniques for Prostate Cancer Dose Escalation and Brachytherapy. 2005 Clin.Oncol. 17-560-571.*
(Continued)

*Primary Examiner* — Tse Chen
*Assistant Examiner* — Patrick M Mehl
(74) *Attorney, Agent, or Firm* — Klarquist Sparkman, LLP

(57) ABSTRACT

A system, method and device for brachytherapy treatment verification is described herein. The verification may be in real time and may provide verification of one or more of dose, source position, dwell time and source activity. In one embodiment the invention provides a method for verifying a brachytherapy radiation treatment including processing a distribution of exposure to a brachytherapy radiation source of a two dimensional imaging array to determine a region of high exposure; obtaining one or more distribution of exposure profiles through the region of high exposure; determining a region of high value in the one or more distribution of exposure profiles; and using the determined region of high exposure and/or high value to calculate one or more brachytherapy radiation source position and/or one or more brachytherapy radiation source distance to thereby verify at least a part of the brachytherapy radiation treatment.

20 Claims, 8 Drawing Sheets

(52) U.S. Cl.
CPC .... *A61N 5/1064* (2013.01); *A61N 2005/1054* (2013.01); *A61N 2005/1072* (2013.01)

(58) Field of Classification Search
USPC .................................................. 600/431, 407
See application file for complete search history.

(56) References Cited

U.S. PATENT DOCUMENTS

| | | |
|---|---|---|
| 6,746,661 B2 | 6/2004 | Kaplan |
| 6,846,282 B1 | 1/2005 | Ford |
| 6,847,838 B1 | 1/2005 | Macey et al. |
| 7,201,715 B2 | 4/2007 | Burdette et al. |
| 7,349,730 B2 | 3/2008 | Ein-Gal |
| 7,554,090 B2 | 6/2009 | Coleman et al. |
| 2004/0006255 A1 | 1/2004 | Sajo et al. |
| 2008/0154086 A1 | 6/2008 | Stubbs |
| 2008/0275341 A1 | 11/2008 | Fehre et al. |
| 2009/0014015 A1 | 1/2009 | Tutar et al. |
| 2009/0121144 A1 | 5/2009 | Black et al. |
| 2009/0198094 A1 | 8/2009 | Fenster et al. |
| 2009/0250602 A1 | 10/2009 | Black et al. |
| 2010/0099985 A1 | 4/2010 | Gueye et al. |
| 2010/0127181 A1 | 5/2010 | Lovoi et al. |
| 2010/0152521 A1 | 6/2010 | Price |

FOREIGN PATENT DOCUMENTS

| | | |
|---|---|---|
| WO | WO 01/60236 A2 | 8/2001 |
| WO | WO 01/64286 A1 | 9/2001 |
| WO | WO 03/062855 A1 | 7/2003 |
| WO | WO 2004/060137 A2 | 7/2004 |
| WO | WO 2005/103762 | 11/2005 |
| WO | WO 2008/009917 A2 | 1/2008 |
| WO | WO 2008/074074 A1 | 6/2008 |
| WO | WO 2008/095257 A1 | 8/2008 |
| WO | WO 2008/145377 A1 | 12/2008 |
| WO | WO 2008/148150 A1 | 12/2008 |

OTHER PUBLICATIONS

Taylor. Illumination Fundamentals. 2000 Lighting Research Center, Rensselaer Polytechnic Institute Chap.3 p. 17-22.*

Khoo. Radiotherapeutic Techniques for Prostate Cancer Dose Escalation and Brachytherapy. 2005 Clin.Oncol. 17:560-571.*

Jain et al. Image Filtering in "MachineVision" 1995 McGraw-Hill Inc, Chapter 4 p. 112-139.*

Majewski et al. Feasibility study of in situ imaging of Ir-192 source during HDR brachytherapy procedure using a small gamma imager based on a Hamamatsu R3292 PSPMT. 1999 IEEE Nuclear Science Symp. 3:1613-1617.*

Groh et al. A performance comparison of flat-panel imager-based MV and kV cone-beam CT. 2002 Med. Phys. 29:967-975.*

Kirkby et al. Consequences of the spectral response of an a-Si EPID and implications for dosimetric calibration. 2005 Med. Phys. 32:2649-2658.*

Nath et al. Dosimetry of interstitial brachytherapy sources: recommendations of the AAPM radiation therapy committee task group No. 43. 1995 Med.Phys. 22:209-234.*

Reniers et al. The radial dose function of low-energy brachytherapy seeds in different solid phantoms. 2004 Phys. Med. Biol. 49:1569-1582.*

UCSF Tutorial on EPID from the UCSF Comprehensive Cancer Center 2008 https://web.archive.org/web/20081005233147/http://radonc.ucsf.edu/research_group/jpouliot/Tutorial/ECH/introduction.htm 1 page.*

Khoo 2005 Clinical Oncology 17:560-571.*

McCurdy et al. 2001 Med.Phys. 28:911-924.*

Menon et al. 2003 Med. Phys. 30:1811-1824.*

Majewski et al., "Feasibility study of in situ imaging of Ir-192 source during HDR brachytheraphy procedure using a small gamma imager based on a Hamamatsu R3292 PSPMT" *IEEE Nuclear Science Symposium*, 3:1613-1617, 1999.

International Search Report, International Application No. PCT/AU2010/001188; Mailing Date: Nov. 4, 2010, 4 pgs.

Written Opinion of the International Searching Authority, International Application No. PCT/AU2010/001188; Mailing Date: Nov. 4, 2010, 6 pgs.

Mock et al., "Portal imaging based definition of the planning target volume during pelvic irradiation for gynecological malignancies," *Int J Radiat Oncol Biol Phys.*, 45(1):227-232, 1999 (Abstract Only).

Vigneault E, et al., "Electronic portal imaging device detection of radioopaque markers for the evaluation of prostate position during megavoltage irradiation: a clinical study," *Int J Radiat Oncol Biol Phys.*, 37(1):205-212, 1997 (Abstract Only).

* cited by examiner (a)

(b)

(a)　　　　　　　　　　(b)

BRACHYTHERAPY DOSE VERIFICATION APPARATUS, SYSTEM AND METHOD

CROSS REFERENCE TO RELATED APPLICATIONS

This is the U.S. National Stage of International Application No. PCT/AU2010/001188, filed Sep. 13, 2010, which was published in English under PCT Article 21(2).

FIELD

THIS INVENTION described herein relates generally to a system, method and device for brachytherapy treatment verification. In particular, the invention is directed to, a system, method and device for real time brachytherapy treatment verification. The treatment verification may be in real time and may provide verification of one or more of dose, source position, dwell time and source activity although the scope of the invention is not necessarily limited thereto.

BACKGROUND

High Dose Rate (HDR) brachytherapy is a form of radiotherapy for cancer treatment that can deliver a high dose of radiation to the target volume, while minimising dose to the nearby healthy tissue. HDR brachytherapy is delivered by one or more high activity sources, moved through catheters placed inside the tumour or close to the treatment volume, dwelling at set positions for specified times.

HDR brachytherapy treatment can be complex, usually requiring computed tomography (CT) data to accurately plan the treatment on a specialised treatment planning system (TPS). The treatment prescription dose can be delivered in single or multiple treatment fractions. Source dwell positions and dwell times are calculated by the TPS to achieve the prescribed dose distribution around the target volume. A remote afterloader unit drives the radioactive source to dwell positions in the implanted catheters, specified by the treatment plan.

Accurate treatment delivery relies on the source dwell positions occurring in the correct locations relative to the surrounding anatomy and according to the approved treatment plan. Inaccuracies in treatment delivery can occur due to several reasons; implanted catheters move inside the patient after CT imaging[1], specified length of the catheter is incorrect, catheter tip offset is incorrect, transfer tube connection is incorrect (afterloader to patient catheter), wrong treatment plan is delivered, remote afterloader malfunctions, source calibration data in the brachytherapy treatment console is incorrect[2].

HDR brachytherapy for prostate cancer, either in combination with external beam radiation therapy (EBRT) or as "monotherapy", has theoretical radiobiological and physics advantages, as well as economic advantages, over EBRT alone for achieving local control for prostate cancer. It is known that "dose-escalation" in the treatment of prostate cancer with radiation improves disease control[3,4]. Progress in escalating dose in HDR treatment has been hampered in comparison to dose-escalation with EBRT—despite putative theoretical advantages—because techniques for real-time individualized treatment verification have been developed for EBRT side by side with the research effort on dose-escalation, thereby enabling certainty about patient safety. Similar standards of verification for HDR brachytherapy would enable economic, radiobiological and physics related advantages of HDR brachytherapy.

Current strategies for HDR treatment verification usually consist of detectors to measure the dose at a single point within the treatment volume. Thermoluminescent dosimeters (TLDs)[5], metal oxide semiconductor field effect transistors[6] (MOSFETs), diodes[7], diamond detectors[8] and scintillation detectors[9,10] are devices that can be used for in vivo dosimetry for brachytherapy. To overcome the limitation of single point detectors, some authors have used sets of detectors to measure a simple dose profile of a few points within the treatment volume[11,12]. A limitation of this method is that the one dimensional profile produced has a low spatial resolution and cannot fully verify the dose distribution delivered to the entire target volume. An additional weakness to point dose methods is the difficulty of localising the detector in relation to the target volume, making dose comparison with the TPS difficult and questionable. Point dose profiles measured inside critical organs often require data profile shifts in order to match measured data with TPS profiles[13]. Detectors have to be placed against or inside the organs, making routine data collection difficult, and causing discomfort to the patient. Establishing a routine in vivo dosimetry protocol for HDR brachytherapy using point detectors is problematic and unlikely to achieve widespread acceptance.

SUMMARY

The present invention is broadly directed to application of a two dimensional imaging array to brachytherapy. In particular the imaging array may provide treatment verification such as one or more of dose verification, source position, dwell time and source activity.

The present inventors have discovered that by using the two dimensional imaging array accurate measurements of dose magnitude, source position and exposure time during treatment can be provided. This is of great advantage and provides treatment verification that is of major importance to health care professionals and allied agencies.

In a first aspect, there is provided a method for verifying a brachytherapy radiation treatment including the steps of:

processing a distribution of exposure to a brachytherapy radiation source of a two dimensional imaging array to determine a region of high exposure;

obtaining one or more distribution of exposure profiles through the region of high exposure;

determining a region of high value in the one or more distribution of exposure profiles; and calculating one or more brachytherapy radiation source position and/or one or more brachytherapy radiation source distance from the determined region of high exposure and/or high value to thereby verify at least a part of the brachytherapy radiation treatment.

According to the first aspect the verification of the brachytherapy radiation treatment may comprise dose verification and/or source position verification.

According to the first aspect the region of high exposure in the distribution of exposure may be determined by (a) a linear search.

According to the first aspect the region of high exposure in the distribution of exposure may be determined by (b) a scanned window approach.

The distribution of exposure profile processed may be for an elapsed time period.

When the distribution of exposure profile is processed for an elapsed time period a dwell time for the brachytherapy radiation source may be calculated.

The dwell time calculated may be for one or more brachytherapy radiation source position.

According to the first aspect the one or more distribution of exposure profiles may comprise one or more orthogonal distribution of exposure profile.

The one or more orthogonal distribution of exposure profiles may comprise a horizontal distribution of exposure profile and/or a vertical distribution of exposure profile.

According to the first aspect the one or more distribution of exposure profiles may comprise one or more profiles other than orthogonal profiles.

According to the first aspect the one or more distribution of exposure profile may comprise multiple profiles either side of the horizontal profile and/or the vertical profile and/or other profiles.

The multiple profiles may comprise two to 100 or more profiles.

In one embodiment the multiple profiles comprise ten profiles.

The method of the first aspect may further include determining a percentage value of the high value in the one or more distribution of exposure profiles.

According to the first aspect the percentage value may be within a range of 0-99% of the maximum value.

The percentage value may be 0, 5, 10, 15, 20, 25, 30, 35, 40, 45, 50, 55, 60, 65, 70, 75, 80, 85, 90, 95 or 99%.

In one embodiment the percentage value is 60%.

In another embodiment the percentage value is 80%.

The method of the first aspect may further include calculating the mid position of the percentage value in the one or more distribution of exposure profiles.

The method of the first aspect may further include mapping the brachytherapy radiation source from the calculated mid position.

The mapping of the brachytherapy radiation source may comprise using a pixel dimension factor to convert a mapped position to a distance unit.

The method of the first aspect may further include filtering the one or more distribution of exposure profiles.

The filtering may be a smoothing filter.

In one embodiment the smoothing filter is a 5×1 pixel median convolution process.

The method of the first aspect may also include a step of dose back projection into a patient volume.

According to the first aspect the dose back projection may comprise a back projection of at least a part of the distribution of exposure.

The back projection of the at least a part of the distribution of exposure may comprise projection of a rayline from one or more pixel in the distribution of exposure.

The back projection may further comprise establishing a dose reconstruction plane within a treated patient volume.

The back projection may further comprise determining a dose at one or more point on the dose reconstruction plane by correcting a rayline dose value.

The correction may be by attenuation, inverse square law and/or photon scatter.

The back projection may comprise multiple dose reconstruction planes to achieve a three dimensional back projected dose distribution.

The method of the first aspect may further include comparing the verified brachytherapy radiation treatment to a planned treatment.

The method of the first aspect may further include generating a report comprising the calculated one or more brachytherapy radiation source positions and/or brachytherapy radiation source distances.

The report may comprise a comparison of the calculated one or more brachytherapy radiation source positions and/or brachytherapy radiation source distances with one or more planned brachytherapy radiation source positions and/or brachytherapy radiation source distances.

The method the first aspect may further comprise a second two dimensional imaging array positioned at an angle to the imaging array.

The method of the first aspect may be a computer method wherein each step is performed by the computer.

In a second aspect there is provided a system for verifying a brachytherapy radiation treatment, the system comprising:

an input for receiving a distribution of exposure to a brachytherapy radiation source of a two dimensional imaging array;

a processor for determining a region of high exposure in the distribution of exposure;

a processor for obtaining one or more distribution of exposure profiles through the region of high exposure;

a processor for determining a region of high value in the one or more distribution of exposure profile; and a processor for calculating one or more brachytherapy radiation source position and/or one or more brachytherapy radiation source distance from the determined region of high value.

According to the second aspect the verification of the brachytherapy radiation treatment may comprise dose verification and/or source position verification.

According to the second aspect the region of high exposure in the distribution of exposure may be determined by (a) a linear search.

According to the second aspect the region of high exposure in the distribution of exposure may be determined by (b) a scanned window approach.

According to the second aspect the one or more distribution of exposure profiles may comprise one or more orthogonal distribution of exposure profile.

The one or more orthogonal distribution of exposure profiles may comprise a horizontal distribution of exposure profile and/or a vertical distribution of exposure profile.

The distribution of exposure profile processed may be for an elapsed time period.

When the distribution of exposure profile is processed for an elapsed time period the system may further comprise a processor for calculating a dwell time for the brachytherapy radiation source.

The dwell time calculated may be for one or more brachytherapy radiation source position.

According to the second aspect the one or more distribution of exposure profiles may comprise one or more profiles other than orthogonal profiles.

According to the second aspect the one or more distribution of exposure profile may comprise multiple profiles either side of the horizontal profile and/or the vertical profile and/or other profiles.

In one embodiment the multiple profiles comprise two to 100 or more profiles.

In one embodiment the multiple profiles comprise ten profiles.

The system of the second aspect may further comprise a processor for determining a percentage value of the high value in the one or more distribution of exposure profiles.

According to the second aspect the percentage value may be within a range of 0-99% of the maximum value.

The percentage value may be 0, 5, 10, 15, 20, 25, 30, 35, 40, 45, 50, 55, 60, 65, 70, 75, 80, 85, 90, 95, 99%.

In one embodiment the percentage value is 60%.

In another embodiment the percentage value is 80%.

The system of the second aspect may further comprise a processor for calculating the mid position of the percentage value in the one or more distribution of exposure profiles.

The system of the second aspect may further comprise a processor for mapping the brachytherapy radiation source from the calculated mid position.

The mapping of the brachytherapy radiation source may further comprise a convertor for using a pixel dimension factor to convert a mapped position to a distance unit.

The system of the second aspect may further comprise a filter for filtering the one or more distribution of exposure profiles.

The filter may be a smoothing filter.

In one embodiment the smoothing filter is a 5×1 pixel median convolution process.

The system of the second aspect may also include a dose back projector for back projecting a dose into a patient volume.

According to the second aspect the dose back projected may comprise at least a part of the distribution of exposure.

The dose back projection of the at least a part of the distribution of exposure may comprise projection of a rayline from one or more pixel in the distribution of exposure.

The dose back projection may further comprise establishing a dose reconstruction plane within a treated patient volume.

The dose back projection may further comprise determining a dose at one or more point on the dose reconstruction plane by correcting a rayline dose value.

The correction may be by attenuation, inverse square law and/or photon scatter.

The dose back projection may comprise multiple dose reconstruction planes to achieve a three dimensional back projected dose distribution.

The system of the second aspect may further include a comparer for comparing the verified brachytherapy radiation treatment to a planned treatment.

The system of the second aspect may further comprise a report generator for generating a report comprising the calculated one or more brachytherapy radiation source positions and/or one or more brachytherapy radiation source distances.

The report may comprise a comparison of the calculated one or more brachytherapy radiation source positions and/or brachytherapy radiation source distances with one or more planned brachytherapy radiation source positions and/or brachytherapy radiation source distances.

The system of the second aspect may further comprise a second processor for receiving a distribution of exposure to the brachytherapy radiation source of second two dimensional imaging array, wherein the second two dimensional imaging array is positioned at an angle to the two dimensional imaging array. When the system of the second aspect comprises a second imaging array the system may process the distribution of exposure of both the two dimensional imaging array and the second two dimensional imaging array.

In a third aspect there is provided a computer program product said computer program product comprising:

a computer usable medium and computer readable program code embodied on said computer usable medium for verifying brachytherapy radiation treatment, the computer readable code comprising:

computer readable program code devices (i) configured to cause the computer to process a distribution of exposure to a brachytherapy radiation source of a two dimensional imaging array to determine a region of high exposure;

computer readable program code devices (ii) configured to cause the computer to obtain one or more distribution of exposure profiles through the region of high exposure;

computer readable program code devices (iii) configured to cause the computer to determine a region of high value in the one or more distribution of exposure profiles; and computer readable program code devices (iv) configured to cause the computer to use the determined region of high value to calculate one or more brachytherapy radiation source position and/or one or more brachytherapy radiation source distance to thereby verify at least a part of the brachytherapy radiation treatment.

According to the third aspect the verification of the brachytherapy radiation treatment may comprise dose verification and/or source position verification.

According to the third aspect the region of high exposure in the distribution of exposure may be determined by (a) a linear search.

According to the third aspect the region of high exposure in the distribution of exposure may be determined by (b) a scanned window approach.

The distribution of exposure profile processed may be for an elapsed time period.

When the distribution of exposure profile is processed for an elapsed time period the computer program product of the third aspect may further comprise computer readable program code devices (v) configured to cause the computer to a calculate a dwell time for the brachytherapy radiation source.

The dwell time calculated may be for one or more brachytherapy radiation source position.

According to the third aspect the one or more distribution of exposure profiles may comprise one or more orthogonal distribution of exposure profile.

The one or more orthogonal distribution of exposure profiles may comprise a horizontal distribution of exposure profile and/or a vertical distribution of exposure profile.

According to the third aspect the one or more distribution of exposure profiles may comprise one or more profiles other than orthogonal profiles.

According to the third aspect the one or more distribution of exposure profile may comprise multiple profiles either side of the horizontal profile and/or the vertical profile and/or other profiles.

The multiple profiles may comprise two to 100 or more profiles

In one embodiment the multiple profiles comprise ten profiles.

The computer program product of the third aspect may further comprise computer readable program code devices (vi) configured to cause the computer to determine a percentage value of the high value in the one or more distribution of exposure profiles.

According to the third aspect the percentage value may be within a range of 0-99% of the maximum value.

The percentage value may be 0, 5, 10, 15, 20, 25, 30, 35, 40, 45, 50, 55, 60, 65, 70, 75, 80, 85, 90, 95 or 99%.

In one embodiment the percentage value is 60%.

In another embodiment the percentage value is 80%.

The computer program product of the third aspect may further comprise computer readable program code devices (vii) configured to cause the computer to calculate the mid position of the percentage value in the one or more distribution of exposure profiles.

The computer program product of the third aspect may further comprise computer readable program code devices (viii) configured to cause the computer to map the brachytherapy radiation source from the calculated mid position.

The mapping of the brachytherapy radiation source may include using a pixel dimension factor to convert a mapped position to a distance unit.

The computer program product of the third aspect may further comprise computer readable program code devices (ix) configured to cause the computer to filter the one or more distribution of exposure profiles.

The filtering may be a smoothing filter.

In one embodiment the smoothing filter is a 5×1 pixel median convolution process.

The computer program product of the third aspect may further comprise computer readable program code devices (x) configured to cause the computer to back project a dose into a patient volume.

According to the third aspect the dose back projection may comprise a back projection of at least a part of the distribution of exposure.

The back projection of the at least a part of the distribution of exposure may comprise projection of a rayline from one or more pixel in the distribution of exposure.

The back projection may further comprise establishing a dose reconstruction plane within a treated patient volume.

The back projection may further comprise determining a dose at one or more point on the dose reconstruction plane by correcting a rayline dose value.

The correction may be by attenuation, inverse square law and/or photon scatter.

The back projection may comprise multiple dose reconstruction planes to achieve a three dimensional back projected dose distribution.

The computer program product of the third aspect may further comprise computer readable program code devices (xi) configured to cause the computer to compare the verified brachytherapy radiation treatment to a planned treatment.

The computer program product of the third aspect may further comprise:

computer readable program code devices (xii) configured to cause the computer to generate a report comprising the calculated one or more brachytherapy radiation source positions and/or brachytherapy radiation source distances.

The report may comprise a comparison of the calculated one or more brachytherapy radiation source positions and/or brachytherapy radiation source distances with one or more planned brachytherapy radiation source positions and/or brachytherapy radiation source distances.

The computer program product of the third aspect may further comprise computer readable program code devices (xiii) configured to cause the computer to process a distribution of exposure to a brachytherapy radiation source of a second two dimensional imaging array to determine a region of high exposure. When the computer program product of the third aspect further comprises computer readable program code devices (xiii) the other computer readable program code devices may cause the computer to process the distribution of exposure of both the two dimensional imaging array and the second two dimensional imaging array.

In a fourth aspect, there is provided a method for determining a brachytherapy source distance from a two dimensional imaging array including the steps of:

processing a distribution of exposure to a brachytherapy radiation source of a two dimensional imaging array to determine a region of high exposure;

determining a curvature parameter that describes or characterises the distribution of the exposure in the region of high exposure; and relating the curvature parameter to calibration data or to a function of the calibration data to thereby determine the brachytherapy source distance from the two dimensional imaging array.

According to the fourth aspect the step of determining the curvature parameter may include:

obtaining one or more distribution of exposure profiles through the region of high exposure; and determining an average width distance at a percentage of an average maximum value for the one or more distribution of exposure profiles.

According to the fourth aspect the curvature parameter may comprise a profile width.

According to the method of the fourth aspect the step of relating the curvature parameter to calibration data may comprise fitting a polynomial function to a calibration function and/or the average width distance at a percentage of an average maximum value for the one or more distribution of exposure profiles.

According to the fourth aspect the one or more distribution of exposure profiles may comprise one or more orthogonal distribution of exposure profiles.

The one or more orthogonal distribution of exposure profiles may comprise a horizontal distribution of exposure profile and/or a vertical distribution of exposure profile.

According to the fourth aspect the one or more distribution of exposure profiles may comprise one or more profiles other than orthogonal profiles.

The one or more distribution of exposure profiles may comprise two to 100 or more profiles In one embodiment the multiple profiles comprise ten profiles.

The method of the fourth aspect may further include determining a percentage value of the region of high value in the one or more distribution of exposure profiles.

According to the fourth aspect the percentage value may be within a range of 0-99% of the maximum value.

The percentage value may be 0, 5, 10, 15, 20, 25, 30, 35, 40, 45, 50, 55, 60, 65, 70, 75, 80, 85, 90, 95 or 99%.

In one embodiment the percentage value is 60%.

In another embodiment the percentage value is 80%.

The method of the fourth aspect may further include calculating the mid position of the percentage value in the one or more distribution of exposure profiles.

The method of the fourth aspect may further include calculating the average mid position of the percentage value in the one or more distribution of exposure profiles.

The method of the fourth aspect may further include mapping the brachytherapy radiation source from the calculated mid position.

The mapping of the brachytherapy radiation source may include using a pixel dimension factor to convert a mapped position to a distance unit.

According to the fourth aspect the step of determining an average width distance at a percentage of the average maximum value may comprise a percentage value in the range of 0 to 99%. The percentage value may be 0, 5, 10, 15, 20, 25, 30, 35, 40, 45, 50, 55, 60, 65, 70, 75, 80, 85, 90, 95 or 99%.

In one embodiment the percentage value is 60%.

In another embodiment the percentage value is 80%.

According to the fourth aspect the step of determining an average width distance at a percentage of the average maximum value may comprise determining the width and/or average of the maximum value in a filtered profile.

According to the fourth aspect the step of determining a curvature parameter may comprise counting the number of pixels comprised in a region enclosed by a boundary determined from the percentage of the average maximum value.

According to the fourth aspect the step of determining a curvature parameter may comprise counting a number of pixels included along a boundary determined from the percentage of the average maximum value.

According to the fourth aspect the step of determining a curvature parameter may comprise fitting a function to a quasi-spherical fluence distribution of the distribution of exposure so that the fit converges to one or more fitting parameter that can be related unambiguously to the distance between the brachytherapy radiation source and the imaging array.

The method of the fourth aspect may further include a step of acquiring one or more image to establish the calibration function that relates an acquired image characteristic to the brachytherapy radiation source distance from the imaging array.

According to the fourth aspect the one or more image may be acquired over a range of distances from the imaging array.

According to the fourth aspect the range may be 10 mm to 1000 mm.

The range may be 15 to 500 mm.

In one embodiment the range is 20 to 300 mm.

According to the fourth aspect the step of acquiring one or more image may comprise sandwiching the brachytherapy radiation source between one or more slab of water equivalent phantom.

According to the fourth aspect the distance between the brachytherapy radiation source and the imaging array may be increased by adding slabs of water equivalent phantom.

The slabs of water equivalent phantom may be 1-20 mm thick. In one embodiment the slabs of water are 10 mm thick.

The method of the fourth aspect may further include filtering the one or more distribution of exposure profile.

The filtering may be a smoothing filter.

In one embodiment the smoothing filter is a 5×1 pixel median convolution process.

The method of the fourth aspect may further include comparing the verified brachytherapy radiation treatment to a planned treatment.

The method of the fourth aspect may further include generating a report comprising the determined brachytherapy source distance.

The method of the fourth aspect may be a computer method wherein each step is performed by the computer.

In a fifth aspect there is provided a system for determining a brachytherapy source distance from a two dimensional imaging array comprising:

a processor for processing a distribution of exposure to a brachytherapy radiation source of a two dimensional imaging array to determine a region of high exposure;

a processor for determining a curvature parameter that describes or characterises the distribution of the exposure in the region of high exposure; and a processor for relating the curvature parameter to calibration data or to a function of the calibration data to thereby determine the brachytherapy source distance from the two dimensional imaging array.

According to the fifth aspect the curvature parameter may comprise a profile width.

According to the fifth aspect the determination of the curvature parameter may include:

obtaining one or more distribution of exposure profiles through the region of high exposure and;

determining an average width distance at a percentage of an average maximum value for the one or more distribution of exposure profiles.

According to the system of the fifth aspect the relating the curvature parameter to calibration data may comprise fitting a polynomial function to a calibration function and/or the average width distance at a percentage of an average maximum value for the one or more distribution of exposure profiles.

According to the fifth aspect the one or more distribution of exposure profiles may comprise one or more orthogonal distribution of exposure profiles.

The one or more orthogonal distribution of exposure profiles may comprise a horizontal distribution of exposure profile and/or a vertical distribution of exposure profile.

According to the fifth aspect the one or more distribution of exposure profiles may comprise one or more profiles other than orthogonal profiles.

The one or more distribution of exposure profiles may comprise two to 100 or more profiles In one embodiment the multiple profiles comprise ten profiles.

The system of the fifth aspect may further comprise a processor for determining a percentage value of the region of high value in the one or more distribution of exposure profiles.

According to the fifth aspect the percentage value may be within a range of 0-99% of the maximum value.

The percentage value may be 0, 5, 10, 15, 20, 25, 30, 35, 40, 45, 50, 55, 60, 65, 70, 75, 80, 85, 90, 95 or 99%.

In one embodiment the percentage value is 60%.

In another embodiment the percentage value is 80%.

The system of the fifth aspect may further comprise a calculator for calculating the mid position of the percentage value in the one or more distribution of exposure profiles.

The system of the fifth aspect may further comprise a calculator for calculating the average mid position of the percentage value in the one or more distribution of exposure profiles.

The system of the fifth aspect may further comprise a processor for mapping the brachytherapy radiation source from the calculated mid position.

The mapping of the brachytherapy radiation source may include using a pixel dimension factor to convert a mapped position to a distance unit.

According to the fifth aspect the step of determining an average width distance at a percentage of the average maximum value may comprise a percentage value in the range of 0 to 99%. The percentage value may be 0, 5, 10, 15, 20, 25, 30, 35, 40, 45, 50, 55, 60, 65, 70, 75, 80, 85, 90, 95 or 99%.

In one embodiment the percentage value is 60%.

In another embodiment the percentage value is 80%.

According to the fifth aspect the step of determining an average width distance at a percentage of the average maximum value may comprise determining the width and/or average of the maximum value in a filtered profile.

According to the fifth aspect the step of determining a curvature parameter may comprise counting the number of pixels comprised in a region enclosed by a boundary determined from the percentage of the average maximum value.

According to the fifth aspect the step of determining a curvature parameter may comprise counting a number of pixels included along a boundary determined from the percentage of the average maximum value.

According to the fifth aspect the step of determining a curvature parameter may comprise fitting a function to a quasi-spherical fluence distribution of the distribution of exposure so that the fit converges to one or more fitting parameter that can be related unambiguously to the distance between the brachytherapy radiation source and the imaging array.

The system of the fifth aspect may further comprise an image acquirer for acquiring one or more image to establish the calibration function that relates an acquired image characteristic to the brachytherapy radiation source distance from the imaging array.

According to the fifth aspect the one or more image may be acquired over a range of distances from the imaging array.

According to the fifth aspect the range may be 10 mm to 1000 mm.

The range may be 15 to 500 mm.

In one embodiment the range is 20 to 300 mm.

According to the fifth aspect the step of acquiring one or more image may comprise sandwiching the brachytherapy radiation source between one or more slab of water equivalent phantom.

According to the fifth aspect the distance between the brachytherapy radiation source and the imaging array may be increased by adding slabs of water equivalent phantom.

The slabs of water equivalent phantom may be 1-20 mm thick.

In one embodiment the slabs of water are 10 mm thick.

The system of the fifth aspect may further comprise a filter for filtering the one or more distribution of exposure profile.

The filtering may be a smoothing filter.

In one embodiment the smoothing filter is a 5×1 pixel median convolution process.

The system of the fifth aspect may further comprise a comparer for comparing the verified brachytherapy radiation treatment to a planned treatment.

The system of the fifth aspect may comprise include a report generator for generating a report comprising the determined brachytherapy source distance.

In a sixth aspect there is provided a computer program product said computer program product comprising:

a computer usable medium and computer readable program code embodied on said computer usable medium for determining a brachytherapy source distance from a two dimensional imaging array, the computer readable code comprising:

computer readable program code devices (i) configured to cause the computer to process a distribution of exposure to the brachytherapy radiation source of the two dimensional imaging array to determine a region of high exposure;

computer readable program code devices (ii) configured to cause the computer to determine a curvature parameter that describes or characterises the distribution of exposure in the region of high exposure; and computer readable program code devices (iii) configured to cause the computer to relate the curvature parameter to calibration data or to a function of the calibration data to thereby determine the brachytherapy source distance from the two dimensional imaging array.

According to the sixth aspect the curvature parameter may comprise a profile width.

According to the sixth aspect the determination of the curvature parameter may include:

obtaining one or more distribution of exposure profiles through the region of high exposure and;

determining an average width distance at a percentage of an average maximum value for the one or more distribution of exposure profiles.

According to the sixth aspect the relating the curvature parameter to calibration data may comprise fitting a polynomial function to a calibration function and/or the average width distance at a percentage of an average maximum value for the one or more distribution of exposure profiles.

According to the sixth aspect the one or more distribution of exposure profiles may comprise one or more orthogonal distribution of exposure profiles.

The one or more orthogonal distribution of exposure profiles may comprise a horizontal distribution of exposure profile and/or a vertical distribution of exposure profile.

According to the sixth aspect the one or more distribution of exposure profiles may comprise one or more profiles other than orthogonal profiles.

The one or more distribution of exposure profiles may comprise two to 100 or more profiles In one embodiment the multiple profiles comprise ten profiles.

The computer program product of the sixth aspect may further comprise computer readable program code devices (iv) configured to cause the computer to determine a percentage value of the region of high value in the one or more distribution of exposure profiles.

According to the sixth aspect the percentage value may be within a range of 0-99% of the maximum value.

The percentage value may be 0, 5, 10, 15, 20, 25, 30, 35, 40, 45, 50, 55, 60, 65, 70, 75, 80, 85, 90, 95 or 99%.

In one embodiment the percentage value is 60%.

In another embodiment the percentage value is 80%.

The computer program product of the sixth aspect may further comprise computer readable program code devices (v) configured to cause the computer to calculate the mid position of the percentage value in the one or more distribution of exposure profiles.

The computer program product of the sixth aspect may further comprise computer readable program code devices (vi) configured to cause the computer to calculate the average mid position of the percentage value in the one or more distribution of exposure profiles.

The computer program product of the sixth aspect may further comprise computer readable program code devices (vii) configured to cause the computer to map the brachytherapy radiation source from the calculated mid position.

The mapping of the brachytherapy radiation source may include using a pixel dimension factor to convert a mapped position to a distance unit.

According to the sixth aspect the determining of the average width distance at a percentage of the average maximum value may comprise a percentage value in the range of 0 to 99%. The percentage value may be 0, 5, 10, 15, 20, 25, 30, 35, 40, 45, 50, 55, 60, 65, 70, 75, 80, 85, 90, 95 or 99%.

In one embodiment the percentage value is 60%.

In another embodiment the percentage value is 80%.

According to the sixth aspect the determination of the average width distance at a percentage of the average maximum value may comprise determining the width and/or average of the maximum value in a filtered profile.

According to the sixth aspect the determination of the curvature parameter may comprise counting the number of pixels comprised in a region enclosed by a boundary determined from the percentage of the average maximum value.

According to the sixth aspect the determination of the curvature parameter may comprise counting a number of pixels included along a boundary determined from the percentage of the average maximum value.

According to the sixth aspect the determination of the curvature parameter may comprise fitting a function to a quasi-spherical fluence distribution of the distribution of exposure so that the fit converges to one or more fitting parameter that can be related unambiguously to the distance between the brachytherapy radiation source and the imaging array.

The computer program product of the sixth aspect may further comprise computer readable program code devices (viii) configured to cause the computer to acquire one or more image to establish the calibration function that relates an acquired image characteristic to the brachytherapy radiation source distance from the imaging array.

According to the sixth aspect the one or more images may be acquired over a range of distances from the imaging array.

According to the sixth aspect the range may be 10 mm to 1000 mm.

The range may be 15 to 500 mm.

In one embodiment the range is 20 to 300 mm.

According to the sixth aspect the acquisition of the one or more images may comprise sandwiching the brachytherapy radiation source between one or more slab of water equivalent phantom.

According to the sixth aspect the distance between the brachytherapy radiation source and the imaging array may be increased by adding slabs of water equivalent phantom.

The slabs of water equivalent phantom may be 1-20 mm thick. In one embodiment the slabs of water are 10 mm thick.

The computer program product of the sixth aspect may further comprise computer readable program code devices (ix) configured to cause the computer to filter the one or more distribution of exposure profile.

The filtering may be a smoothing filter.

In one embodiment the smoothing filter is a 5×1 pixel median convolution process.

The computer program product of the sixth aspect may further comprise computer readable program code devices (x) configured to cause the computer to compare the verified brachytherapy radiation treatment to a planned treatment.

The computer program product of the sixth aspect may further comprise computer readable program code devices (xi) configured to cause the computer to generate a report comprising the determined brachytherapy source distance.

In a seventh aspect there is provided a method of calibrating a brachytherapy radiation dosage including the steps of:

exposing a two dimensional imaging array to a brachytherapy radiation source to obtain a measured response;

associating the measured response of the imaging array to the brachytherapy radiation source to a known dosage;

determining the brachytherapy radiation source position using the method of the first aspect;

determining a response of the imaging array by calculating an average pixel value for a region of interest of one or more pixels surrounding the determined source position;

fitting the determined response and/or the known dosage to calculate a dose rate response function for each distance in a set of brachytherapy radiation source distances; and applying the calculated dose rate response function to the brachytherapy radiation dosage detected by the imaging array to calibrate the detected brachytherapy radiation dosage.

The method of the seventh aspect may further include inserting a phantom of water or a material to approximate biological tissue between the brachytherapy radiation source and the imaging array.

According to the method of the seventh aspect the step of associating the measured response may include direct measurement with another calibrated dosimeter and/or analytical calculation.

The analytical calculation may be by a treatment planning system and/or Monte Carlo radiation transport modelling.

According to the method of the seventh aspect the exposing may comprise exposing with different brachytherapy radiation source activities and/or exposing with time dependent decay.

According to the method of the seventh aspect the calculated dose rate response function may comprise an analytical function and/or a lookup table.

The method of the seventh aspect may further include the step of generating a report comprising the calibrated detected brachytherapy radiation dosage.

The method of the seventh aspect may be a computer method wherein each step is performed by the computer.

In an eighth aspect there is provided a system of calibrating a brachytherapy radiation dosage comprising:

a two dimensional imaging array for exposure to a brachytherapy radiation source to obtain a measured response;

a processor for associating the measured response of the imaging array to the brachytherapy radiation source to a known dosage;

a processor for determining the brachytherapy radiation source position using the method of the first aspect;

a calculator for determining a response of the imaging array by calculating an average pixel value for a region of interest of one or more pixels surrounding the determined source position;

a processor for fitting the determined response and/or the known dosage to calculate a dose rate response function for each distance in a set of brachytherapy radiation source distances; and a processor for applying the calculated dose rate response function to the brachytherapy radiation dosage detected by the imaging array to calibrate the detected brachytherapy radiation dosage.

The system of the eighth aspect may further comprise an approximator for inserting a phantom of water or a material to approximate biological tissue between the brachytherapy radiation source and the imaging array.

According to the system of the eighth aspect the associating of the measured response may include direct measurement with another calibrated dosimeter and/or analytical calculation.

The analytical calculation may be by a treatment planning system and/or Monte Carlo radiation transport modelling.

According to the system of the eighth aspect the exposure may comprise exposure with different brachytherapy radiation source activities and/or exposing with time dependent decay.

According to the system of the eighth aspect the calculated dose rate response function may comprise an analytical function and/or a lookup table.

The system of the eighth aspect may further include a report generator for generating a report comprising the calibrated detected brachytherapy radiation dosage.

In a ninth aspect there is provided a computer program product said computer program product comprising:

a computer usable medium and computer readable program code embodied on said computer usable medium for calibrating a brachytherapy radiation dosage, the computer readable code comprising:

computer readable program code devices (i) configured to cause the computer to expose a two dimensional imaging array to a brachytherapy radiation source to obtain a measured response;

computer readable program code devices (ii) configured to cause the computer to associate the measured response of the imaging array to the brachytherapy radiation source to a known dosage;

computer readable program code devices (iii) configured to cause the computer to determine the brachytherapy radiation source position using the method of the first aspect;

computer readable program code devices (iv) configured to cause the computer to determine a response of the imaging array by calculating an average pixel value for a region of interest of one or more pixels surrounding the determined source position;

computer readable program code devices (v) configured to cause the computer to fit the determined response and/or the known dosage to calculate a dose rate response function for each distance in a set of brachytherapy radiation source distances; and computer readable program code devices (vi) configured to cause the computer to apply the calculated dose rate response function to the brachytherapy radiation dosage detected by the imaging array to calibrate the detected brachytherapy radiation dosage.

The computer program product of the ninth aspect may further comprise computer readable program code devices (vii) configured to cause the computer to insert a phantom of water or a material to approximate biological tissue between the brachytherapy radiation source and the imaging array.

According to the computer program product of the ninth aspect the step of associating the measured response may include direct measurement with another calibrated dosimeter and/or analytical calculation.

The analytical calculation may be by a treatment planning system and/or Monte Carlo radiation transport modelling.

According to the computer program product of the ninth aspect the exposing may comprise exposing with different brachytherapy radiation source activities and/or exposing with time dependent decay.

According to the computer program product of the ninth aspect the calculated dose rate response function may comprise an analytical function and/or a lookup table.

The computer program product of the ninth aspect may further comprise computer readable program code devices (viii) configured to cause the computer to generate a report comprising the calibrated detected brachytherapy radiation dosage.

In a tenth aspect there is provided a method for determining a geometric relationship between a brachytherapy radiation source and a brachytherapy implant or a brachytherapy patient, the method including the steps of:

inserting one or more x-ray marker device into the brachytherapy implant;

acquiring images of the brachytherapy implant using an external x-ray unit and a two dimensional imaging array;

calculating the position of the brachytherapy implant relative to the imaging array from the acquired images to thereby determine the geometric relationship between the brachytherapy radiation source and the brachytherapy implant or brachytherapy patient.

According to the method of the tenth aspect the imaging array may be located in a position used during brachytherapy radiation treatment.

The method of the tenth aspect may also include the steps of delivering brachytherapy treatment and recording brachytherapy radiation source positions.

According to the method of the tenth aspect the recorded source positions may be referenced to the brachytherapy implant positions.

The brachytherapy implant positions may be confirmed and/or compared to a treatment planning system.

According to the method of the tenth aspect the brachytherapy implant may be inserted in the brachytherapy patient.

According to the tenth aspect the method may further include determining the location of the brachytherapy implant relative to one or more fiducial markers implanted in a vicinity of a treatment area.

According to the method of the tenth aspect the brachytherapy implant may be a catheter and/or application channel.

According to the tenth aspect the calculated position may be the position in three dimensions of the brachytherapy implant or the brachytherapy patient relative to the imaging array.

In an eleventh aspect there is provided a system for determining a geometric relationship between a brachytherapy radiation source and a brachytherapy implant or a brachytherapy patient, the system comprising:

a brachytherapy implant comprising one or more x-ray marker device;

an external x-ray unit and a two dimensional imaging array for acquiring images of the brachytherapy implant;

a processor for calculating the position of the brachytherapy implant relative to the imaging array from the acquired images to thereby determine the geometric relationship between the brachytherapy radiation source and the brachytherapy implant or brachytherapy patient.

According to the system of the eleventh aspect the imaging array may be located in a position used during brachytherapy radiation treatment.

The system of the eleventh aspect may also comprise a recorder for recording brachytherapy radiation source positions during delivery of brachytherapy treatment.

The system of the eleventh aspect may further comprise a referencer for referencing the recorded source positions to the brachytherapy implant positions.

The system of the eleventh aspect may further comprise a processor for confirming and/or comparing the calculated brachytherapy implant position to a treatment planning system.

According to system method of the eleventh aspect the brachytherapy implant may be inserted in the brachytherapy patient.

According to the eleventh aspect the system may further comprise one or more processor for determining a location of the brachytherapy implant relative to one or more fiducial markers implanted in a vicinity of a treatment area.

According to the system of the eleventh aspect the brachytherapy implant may be a catheter and/or application channel.

According to the eleventh aspect the calculated position may be the position in three dimensions of the brachytherapy implant or the brachytherapy patient relative to the imaging array.

In a twelfth aspect there is provided a computer program product said computer program product comprising:

a computer usable medium and computer readable program code embodied on said computer usable medium for determining a geometric relationship between a brachytherapy radiation source and a brachytherapy implant or a brachytherapy patient, the computer readable code comprising:

computer readable program code devices (i) configured to cause the computer to acquire images of the brachytherapy implant using an external x-ray unit and a two dimensional imaging array wherein the brachytherapy implant comprises one or more x-ray marker device;

computer readable program code devices (ii) configured to cause the computer to calculate the position of the brachytherapy implant relative to the imaging array from the acquired images to thereby determine the geometric relationship between the brachytherapy radiation source and the brachytherapy implant or brachytherapy patient.

The computer program product of the twelfth aspect may further comprise computer readable program code devices (iii) configured to cause the computer to deliver brachytherapy treatment and/or (iv) configured to record brachytherapy radiation source positions.

According to the computer program product of the twelfth aspect the recorded source positions may be referenced to the brachytherapy implant positions.

The computer program product of the twelfth aspect may further comprise computer readable program code devices (v) configured to cause the computer to confirm and/or compare the calculated brachytherapy implant position to a treatment planning system.

According to the twelfth aspect the brachytherapy implant may be inserted in the brachytherapy patient.

According to the tenth aspect the computer program product code of the twelfth aspect may further comprise computer readable program code devices (vi) configured to cause the computer to determine a location of the fiducial markers relative to one or more fiducial markers implanted in a vicinity of a treatment area.

According to the twelfth aspect the brachytherapy implant may be a catheter and/or application channel.

According to the twelfth aspect the calculated position may be the position in three dimensions of the brachytherapy implant or the brachytherapy patient relative to the imaging array.

As used herein, except where the context requires otherwise, the term "comprise" and variations of the term, such as "comprising", "comprises" and "comprised", are not intended to exclude further additives, components, integers or steps.

DETAILED DESCRIPTION

Figure 1A:
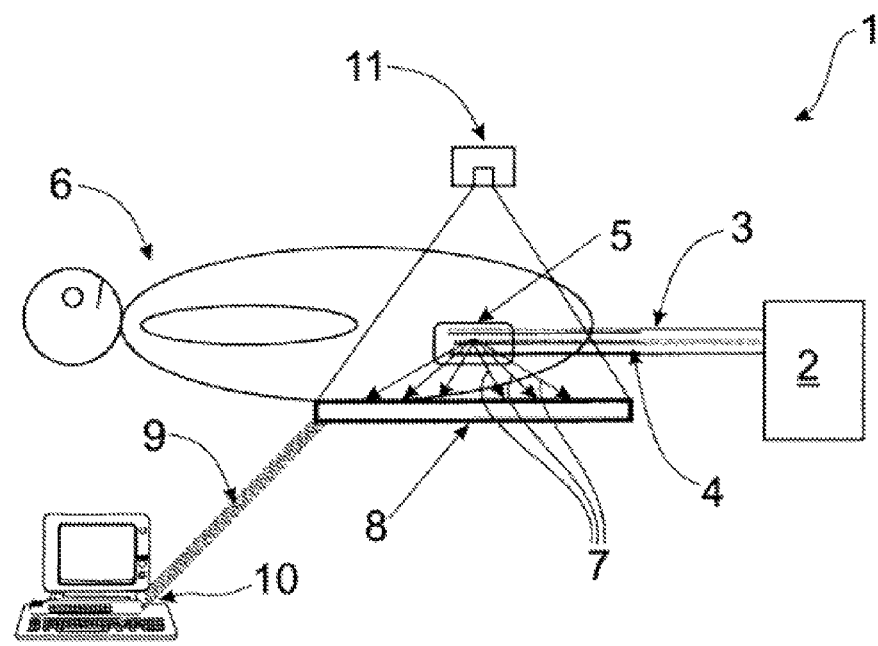
FIG. 1a: shows one embodiment of a system according to the invention.

The inventors have provided novel and inventive methods, systems and devices for brachytherapy utilising a two dimensional imaging array. The present inventors have discovered that by using the two dimensional array accurate measurements of both dose magnitude and source location during treatment can be provided. Such measurements are of great importance to a patient undergoing brachytherapy and great advantage of significant importance to health care professionals and allied agencies.

As used herein, unless the context suggests otherwise, the term external means external to the brachytherapy patient and the term internal means internal to the brachytherapy patient.

The imaging array is preferably sensitive to high dose rate (HDR), low dose rate (LDR) and pulsed dose rate (PDR) treatment afterloader isotopes for brachytherapy. The range of sensitivity covers the typical HDR and LDR dose rates for brachytherapy isotope sources, which is 0-10 cGy/s at the detector surface.

The array detection area may be large enough to encompass the full dimension of typical clinical HDR brachytherapy (HDRb) implants. The detection area of the array may be 50-1000×50-1000 mm. In one embodiment the area is 400×300 mm² detection area (512×384 pixels), The array has the capability to acquire images when activated from an external trigger source, may be triggered manually or coupled to an afterloader device signal or other functionality.

Suitably the array pixel array framerate is in the range of approximately 10 to 500 ms. In other embodiments the framerate may be in the range of approximately 50 to 150 ms or 100 to 130 ms. The pixel array framerate may be approximately 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495 or 500 ms. In one embodiment the pixel array framerate is approximately 116 ms.

Preferably the imager control unit stores multiple frames, not just the average of frames over the acquisition period.

In one particular embodiment the array is an electronic portal imaging device (EPID). The inventors have shown that EPID dose-response characteristics are suitable for HDRb. These include reproducibility, sensitivity to dose increments in exposure and sensitivity to acquisition time increments, and source position displacements. The EPID response was also assessed for the range of typical HDRb photon energies. A solid-water phantom was used to calibrate the EPID for exit dose and a simple treatment plan was verified. Reproducibility was within 1.8% (1SD) over 6 months. The EPID response was linear (2%) for both exposure and acquisition time (0.1-1000 s). Source position errors could be distinguished to 1 mm (smallest source steps=2.5 mm). The EPID signal correlated well with time error ($R^2$=0.96), 0.98% signal change per 1% time change, over 5-20 s. All typical radiotherapy photon energies 50 kV-18 MV, that are amenable to dosimetry with an external detector/dosimetry system. Typical HDRb photon energies, primary and scattered, have explicitly been investigated. The EPID energy-response was non-linear, with an over-response to low energies (peak at ~100 keV). For the simple treatment plan, a profile parallel to the catheter axis showed an average agreement of 1.6%±0.9% (1SD), with a maximum difference of 3.3% between EPID and TPS. EPID images are therefore sensitive to real-time source position and dwell time errors in a phantom. With the addition of CT information, this system has the potential to reveal previously unidentified in-treatment errors in HDR brachytherapy for patients.

In one embodiment the EPID is an aSi EPID (IAS 11-19, Varian Medical Systems, Palo Alto, Calif., USA) operated using the AM Maintenance software module (v7.1.2003.905) having a 400×300 mm² detection area (512×384 pixels), a 1 mm Cu build-up layer, a phosphor screen and a hydrogenated a-Si:H photodiode array.

The dose measured by the EPID may be used to predict the dose at a location within the patient or phantom. Amorphous silicon (a-Si) imagers have the advantage of high resolution, good image quality, and require less patient dose for the same image quality, compared to other types of EPIDs. Their dose-response characteristics have been determined for the megavoltage range, but have not been documented for an Ir192 HDR brachytherapy source.

There are major differences to be expected between conventional EBRT and the present invention's provision of brachytherapy EPID dose verification. Instead of an x-ray beam with on- and off-times, an exposure from a brachytherapy source is continuous, made discrete by the loading procedure.

One embodiment of an apparatus 1 for use in the invention is shown in FIG. 1a. Apparatus 1 includes a brachytherapy afterloader 2 which propels a brachytherapy radiation source 3 into one or more implanted catheters 4 so as to expose a patient or subject volume, which in this embodiment is a cancer site 5, internal patient 6 to the brachytherapy radiation source radiation. The exit radiation 7 is detected by the imaging array 8. The imaging array 8 is connected through communications network 9 to a control system or computer 10. Apparatus 1 also includes an external x-ray system 11 for use in determining geometric relationships as explained below.

FIG. 1 shows an arrangement particularly useful for verifying the treatment of prostate cancer. The invention is not limited to prostate cancer and may be used in the verification of treatment of any cancer or other disease or condition responsive to a brachytherapy source.

In another embodiment the invention may comprise a second imaging array (not shown) at an angle to the first imaging array 8. In this embodiment the distance of the source from the first 8 and/or second imaging array may be determined by a re-application of the methods described herein.

The second imaging array may be at any angle to the first imaging array. In one embodiment the second imaging array is at a right angle to the first imaging array 8.

Figure 1B:
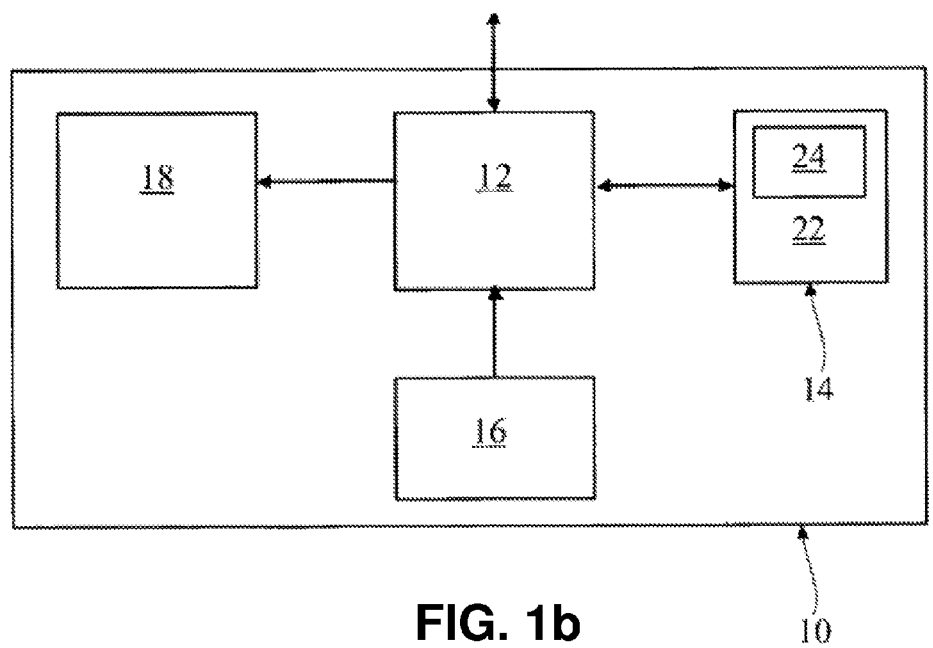
FIG. 1b: shows one embodiment of a computer for use with the invention.

With reference to FIG. 1b, one embodiment of control system or computer 10 is illustrated. As shown, system 10 comprises a processor 12 operatively coupled to a storage medium in the form of a memory 14. One or more input device 16, such as imaging array 8, a keyboard, mouse and/or pointer, is operatively coupled to the processor 12 and one or more output device 18, such as a computer screen and/or report generator, is operatively coupled to the processor 12.

Memory 14 comprises a computer or machine readable medium 22, such as a read only memory (e.g., programmable read only memory (PROM), or electrically erasable programmable read only memory (EEPROM)), a random access memory (e.g. static random access memory (SRAM), or synchronous dynamic random access memory (SDRAM)), or hybrid memory (e.g., FLASH), or other types of memory as is well known in the art. The computer readable medium 22 comprises computer readable program code components 24 for performing the methods in accordance with the teachings of the present invention, at least some of which are selectively executed by the processor 12 and are configured to cause the execution of the embodiments of the present invention described herein. Hence, the machine readable medium 22 may have recorded thereon a program of instructions for causing the machine 10 to perform the methods in accordance with embodiments of the present invention described herein.

Through the use of a two dimensional imaging array the present invention may provide brachytherapy treatment verification in real time and may provide verification of one or more of dose, source position, dwell time and/or source activity. The treatment may be HDR brachytherapy treatment.

The EPID may be characterised for use with an Ir192 HDR brachytherapy source. An EPID image, of delivered dose, may be directly compared to the dose predicted by the TPS. It is shown that EPID images can verify source dwell positions and dwell times with sufficient resolution to identify most classes of setup and treatment delivery errors. This provides the physicist and radiation oncologist with a quality assurance measure of absolute dose as well as the geometrical distribution of the delivered dose, which is not possible with any current HDR brachytherapy dosimetry system.

In one aspect the invention provides a method for verifying a brachytherapy radiation treatment.

One step of method may be to process a distribution of exposure to a brachytherapy radiation source of a two dimensional imaging array to determine a region of high exposure. Any suitable method for determining the region of high exposure may be use.

In one embodiment the region of high exposure in the distribution of exposure is determined by (a) a linear search. The linear search may be through the imager array elements. The linear search may comprise a temporary pointer updated to the 'maximum so far' element at each step.

In another embodiment the region of high exposure is determined by (b) a scanned window approach. In the scanned window approach the value compared at each step through the array may be an average of the pixel values in the immediate neighborhood. The immediate neighborhood may be a window of pixel regions centred at the current pixel. The window may be 3 to 51 pixels. In other embodiments the window may be 5 to 21 pixels or 7 to 15 pixels. The window may be 3, 5, 7, 9, 11, 13, 15, 17, 19, 21, 23, 25, 27, 29, 31, 33, 35, 37, 39, 41, 43, 45, 47, 49 or 51 pixels.

Another step of the method may be obtaining one or more distribution of exposure profiles through the region of high exposure.

The one or more distribution of exposure profiles may comprise one or more orthogonal distribution of exposure profile. The one or more orthogonal distribution of exposure profiles may comprise a horizontal distribution of exposure profile and/or a vertical distribution of exposure profile.

The one or more distribution of exposure profile may comprise one or more profile other than orthogonal profiles.

The one or more distribution of exposure profile may comprise multiple profiles either side of the horizontal profile and/or the vertical profile and/or other profiles. The multiple profiles may comprise two to 100 or more profiles. In one embodiment the multiple profiles comprises 5 to 20 profiles. In a particular embodiment the multiple profiles comprise ten profiles.

The method may also include a step of determining a region of high value in the one or more distribution of exposure profiles.

Another step in the method may be calculating one or more brachytherapy radiation source position and/or one or more brachytherapy radiation source distance from the determined region of high exposure and/or high value to thereby verify at least a part of the brachytherapy radiation treatment.

The verification in the method may comprise dose verification and/or source position verification.

The distribution of exposure profile processed may be for an elapsed time period. The elapsed time period may be the duration of the brachytherapy treatment. Based on the teachings herein a skilled person is readily able to select a suitable elapsed time period.

The invention is particularly advantageous because when the distribution of exposure profile is processed for an elapsed time period, a dwell time for the brachytherapy radiation source may be calculated. A further advantage is that the dwell time calculated may be for one or more brachytherapy radiation source position.

The method may further include calculating the mid position of the percentage value in the one or more distribution of exposure profiles. The calculated mid position may be used to map the brachytherapy radiation source. The mapping of the brachytherapy radiation source may comprise using a pixel dimension factor to convert a mapped position to a distance unit.

The method may further include filtering the one or more distribution of exposure profiles. The filtering may be a smoothing filter. In one embodiment the smoothing filter is a 5×1 pixel median convolution process.

Of significant advantage to patients and medical professionals, the method may further include comparing the verified brachytherapy radiation treatment to a planned treatment. This comparison may allow any variation from the planned treatment to be observed. This is particularly valuable when the method is performed in real time as it allows an operator make suitable corrections.

Another advantage of the method is that it may include generating a report comprising the calculated one or more brachytherapy radiation source positions and/or brachytherapy radiation source distances. The report may comprise a comparison of the calculated one or more brachytherapy radiation source positions and/or brachytherapy radiation source distances with one or more planned brachytherapy radiation source positions and/or brachytherapy radiation source distances.

The method may be a computer method wherein each step is performed by the computer 10.

The invention also provides a system for verifying a brachytherapy radiation treatment.

The system may comprise an input for receiving a distribution of exposure to a brachytherapy radiation source of a two dimensional imaging array. The system may also comprise a processor for determining a region of high exposure in the distribution of exposure.

The system may further comprise a processor for obtaining one or more distribution of exposure profiles through the region of high exposure.

The system may also comprise a processor for determining a region of high value in the one or more distribution of exposure profile.

The system may also comprise a processor for calculating one or more brachytherapy radiation source position and/or one or more brachytherapy radiation source distance from the determined region of high value.

The invention also provides a computer program product said computer program product comprising a computer usable medium and computer readable program code embodied on said computer usable medium for verifying brachytherapy radiation treatment.

The computer readable code may comprise computer readable program code devices (i) configured to cause the computer to process a distribution of exposure to a brachytherapy radiation source of a two dimensional imaging array to determine a region of high exposure.

The computer program product may also comprise computer readable program code devices (ii) configured to cause the computer to obtain one or more distribution of exposure profiles through the region of high exposure.

The computer program product may further comprise computer readable program code devices (iii) configured to cause the computer to determine a region of high value in the one or more distribution of exposure profiles.

The computer program product may also comprise computer readable program code devices (iv) configured to cause the computer to use the determined region of high value to calculate one or more brachytherapy radiation source position and/or one or more brachytherapy radiation source distance to thereby verify at least a part of the brachytherapy radiation treatment.

In another aspect the invention provides a method for determining a brachytherapy source distance from a two dimensional imaging array. The method may include the step of processing a distribution of exposure to a brachytherapy radiation source of a two dimensional imaging array to determine a region of high exposure.

The method may also include the step of determining a curvature parameter that describes or characterises the distribution of the exposure in the region of high exposure.

The determining step may include obtaining one or more distribution of exposure profiles through the region of high exposure and determining an average width distance at a percentage of an average maximum value for the one or more distribution of exposure profiles.

The curvature parameter may comprise a profile width.

In one embodiment the determining a curvature parameter comprises counting the number of pixels comprised in a region enclosed by a boundary determined from the percentage of the average maximum value.

In another embodiment the step of determining a curvature parameter comprises counting a number of pixels included along a boundary determined from the percentage of the average maximum value.

In yet another embodiment the determining a curvature parameter comprises fitting a function to a quasi-spherical fluence distribution of the distribution of exposure so that the fit converges to one or more fitting parameter that can be related unambiguously to the distance between the brachytherapy radiation source and the imaging array.

The method may also include relating the curvature parameter to calibration data or to a function of the calibration data to thereby determine the brachytherapy source distance from the two dimensional imaging array.

The function may be a mathematical function or other description or representation of the calibration data. The function may comprise fitting an equation through calibration data and using the equation, or by a look-up table of the calibration data, combined with interpolation.

The determining an average width distance at a percentage of the average maximum value may comprise determining the width and/or average of the maximum value in a filtered profile.

The step of relating the curvature parameter to calibration data may comprise fitting a polynomial function to a calibration function and/or the average width distance at a percentage of an average maximum value for the one or more distribution of exposure profiles.

The one or more distribution of exposure profiles may comprise one or more orthogonal distribution of exposure profiles. The one or more orthogonal distribution of exposure profiles may comprise a horizontal distribution of exposure profile and/or a vertical distribution of exposure profile.

The one or more distribution of exposure profiles may comprise profiles other than orthogonal profiles.

The one or more distribution of exposure profiles may comprise two to 100 or more profiles. In one embodiment the multiple profiles comprises 5 to 20 profiles. In a particular embodiment the multiple profiles comprise ten profiles.

The method may further include determining a percentage value of the region of high value in the one or more distribution of exposure profiles. The percentage value may be within a range of 0-99% of the maximum value. The percentage value may be 0, 5, 10, 15, 20, 25, 30, 35, 40, 45, 50, 55, 60, 65, 70, 75, 80, 85, 90, 95 or 99%. In one embodiment the percentage value is 60%. In another embodiment the percentage value is 80%.

The method may further include calculating the mid position of the percentage value in the one or more distribution of exposure profiles.

The method may further include calculating the average mid position of the percentage value in the one or more distribution of exposure profiles.

The may further include mapping the brachytherapy radiation source from the calculated mid position.

The mapping of the brachytherapy radiation source may include using a pixel dimension factor to convert a mapped position to a distance unit.

The method may further include a step of acquiring one or more image to establish the calibration function that relates an acquired image characteristic to the brachytherapy radiation source distance from the imaging array. The one or more image may be acquired over a range of distances from the imaging array. The range may be 10 mm to 1000 mm or 15 to 500 mm. In one embodiment the range is 20 to 300 mm.

The step of acquiring one or more image may comprise sandwiching the brachytherapy radiation source between one or more slab of water equivalent phantom.

The distance between the brachytherapy radiation source and the imaging array may be increased by adding slabs of water equivalent phantom. The slabs of water equivalent phantom may be 1-20 mm, 5-15 mm or 8-12 mm thick. The slabs may be 1, 2, 3, 4, 5, 6, 7, 8, 9, 10, 11, 12, 13, 14, 15, 16, 17, 18, 19 or 20 mm thick. In one embodiment the slabs of water are 10 mm thick.

The one or more distribution of exposure profile may be filtered. The filter may be a smoothing filter. In one embodiment the smoothing filter is a 5×1 pixel median convolution process.

As already mentioned, the invention is of particular advantage because it allows the verified brachytherapy radiation treatment to be compared to a planned treatment. Further, a report may be generated which comprised the determined brachytherapy source distance and/or the comparison.

The method for determining a brachytherapy source distance may be a computer method wherein each step is performed by the computer.

In invention also provides a system for determining a brachytherapy source distance from a two dimensional imaging array. The system may comprise a processor for processing a distribution of exposure to a brachytherapy radiation source of a two dimensional imaging array to determine a region of high exposure.

The system may also comprise a processor for determining a curvature parameter that describes or characterises the distribution of the exposure in the region of high exposure.

The system may further comprise a processor for relating the curvature parameter to calibration data or to a function of the calibration data to thereby determine the brachytherapy source distance from the two dimensional imaging array.

Also provided by the present invention is a computer program product said computer program product comprising a computer usable medium and computer readable program code embodied on said computer usable medium for determining a brachytherapy source distance from a two dimensional imaging array, the computer readable code comprising computer readable program code devices (i) configured to cause the computer to process a distribution of exposure to the brachytherapy radiation source of the two dimensional imaging array to determine a region of high exposure.

The computer program product may also comprise computer readable program code devices (ii) configured to cause the computer to determine a curvature parameter that describes or characterises the distribution of exposure in the region of high exposure.

The computer program product may further comprise computer readable program code devices (iii) configured to cause the computer to relate the curvature parameter to calibration data or to a function of the calibration data to thereby determine the brachytherapy source distance from the two dimensional imaging array.

The invention also provides a method of calibrating a brachytherapy radiation dosage. The method may include the step of exposing a two dimensional imaging array to a brachytherapy radiation source to obtain a measured response. The exposing may comprise exposing with different brachytherapy radiation source activities and/or exposing with time dependent decay.

The method may also include associating the measured response of the imaging array to the brachytherapy radiation source to a known dosage. The associating the measured response may include direct measurement with another calibrated dosimeter and/or analytical calculation. The analytical calculation may be by a treatment planning system and/or Monte Carlo radiation transport modelling. The method may further include determining the brachytherapy radiation source position using the method of the first aspect.

The method may also include determining a response of the imaging array by calculating an average pixel value for a region of interest of one or more pixels surrounding the determined source position.

The method may also include fitting the determined response and/or the known dosage to calculate a dose rate response function for each distance in a set of brachytherapy radiation source distances. The calculated dose rate response function may comprise an analytical function and/or a lookup table.

The method may also include applying the calculated dose rate response function to the brachytherapy radiation dosage detected by the imaging array to calibrate the detected brachytherapy radiation dosage.

Another step the method of calibrating may also include is inserting a phantom of water or a material to approximate biological tissue between the brachytherapy radiation source and the imaging array.

The method of calibrating may further include the step of generating a report comprising the calibrated detected brachytherapy radiation dosage.

Like the above methods the method of calibrating may be a computer method wherein each step is performed by the computer.

The invention also provides a system of calibrating a brachytherapy radiation dosage. The system may comprise a two dimensional imaging array for exposure to a brachytherapy radiation source to obtain a measured response.

The system may also comprise a processor for associating the measured response of the imaging array to the brachytherapy radiation source to a known dosage.

The system may further comprise a processor for determining the brachytherapy radiation source position using the method of the first aspect.

The system of calibrating may also comprise a calculator for determining a response of the imaging array by calculating an average pixel value for a region of interest of one or more pixels surrounding the determined source position.

The system may also comprise a processor for fitting the determined response and/or the known dosage to calculate a dose rate response function for each distance in a set of brachytherapy radiation source distances.

Also comprised in the system for calibrating may be a processor for applying the calculated dose rate response function to the brachytherapy radiation dosage detected by the imaging array to calibrate the detected brachytherapy radiation dosage.

Also provided by the present invention is a computer program product said computer program product comprising a computer usable medium and computer readable program code embodied on said computer usable medium for calibrating a brachytherapy radiation dosage.

The computer program product may comprise computer readable program code devices (i) configured to cause the computer to expose a two dimensional imaging array to a brachytherapy radiation source to obtain a measured response.

The computer program product may also comprise computer readable program code devices (ii) configured to cause the computer to associate the measured response of the imaging array to the brachytherapy radiation source to a known dosage.

The computer program product may further comprise code devices (iii) configured to cause the computer to determine the brachytherapy radiation source position using the method of the first aspect.

The computer program product may also comprise computer readable program code devices (iv) configured to cause the computer to determine a response of the imaging array by calculating an average pixel value for a region of interest of one or more pixels surrounding the determined source position;

The computer program product may further comprise computer readable program code devices (v) configured to cause the computer to fit the determined response and/or the known dosage to calculate a dose rate response function for each distance in a set of brachytherapy radiation source distances.

Also comprised on the computer program product may be computer readable program code devices (vi) configured to cause the computer to apply the calculated dose rate response function to the brachytherapy radiation dosage detected by the imaging array to calibrate the detected brachytherapy radiation dosage.

The present invention also provides a method for determining a geometric relationship between a brachytherapy radiation source and a brachytherapy implant or a brachytherapy patient.

The method may include the steps of inserting one or more x-ray marker device into the brachytherapy implant.

The method for determining a geometric relationship may also include acquiring images of the brachytherapy implant using an external x-ray unit and a two dimensional imaging array.

The method for determining a geometric relationship may further include calculating the position of the brachytherapy implant relative to the imaging array from the acquired images to thereby determine the geometric relationship between the brachytherapy radiation source and the brachytherapy implant or brachytherapy patient.

The calculated position may be the position in three dimensions of the brachytherapy implant or the brachytherapy patient relative to the imaging array.

According to the method for determining a geometric relationship the imaging array may be located in a position used during brachytherapy radiation treatment.

The method may also include the steps of delivering brachytherapy treatment and recording brachytherapy radiation source positions. The recorded source positions may be referenced to the brachytherapy implant positions.

In one particularly advantageous embodiment the brachytherapy implant positions may be confirmed and/or compared to a treatment planning system.

According to the tenth aspect the method may further include determining the location of the brachytherapy implant relative to one or more fiducial markers implanted in a vicinity of a treatment area.

The brachytherapy implant may be a catheter and/or application channel.

The invention also provides a system for determining a geometric relationship between a brachytherapy radiation source and a brachytherapy implant or a brachytherapy patient.

The system may comprise a brachytherapy implant comprising one or more x-ray marker device.

The system may also comprise an external x-ray unit and a two dimensional imaging array for acquiring images of the brachytherapy implant.

The system may further comprise a processor for calculating the position of the brachytherapy implant relative to the imaging array from the acquired images to thereby determine the geometric relationship between the brachytherapy radiation source and the brachytherapy implant or brachytherapy patient.

The present invention also provides a computer program product said computer program product comprising a computer usable medium and computer readable program code embodied on said computer usable medium for determining a geometric relationship between a brachytherapy radiation source and a brachytherapy implant or a brachytherapy patient.

The computer program product may comprise computer readable program code devices (i) configured to cause the computer to acquire images of the brachytherapy implant using an external x-ray unit and a two dimensional imaging array wherein the brachytherapy implant comprises one or more x-ray marker device.

The computer program product may also comprise computer readable program code devices (ii) configured to cause the computer to calculate the position of the brachytherapy implant relative to the imaging array from the acquired images to thereby determine the geometric relationship between the brachytherapy radiation source and the brachytherapy implant or brachytherapy patient.

According to the invention the response of the detector to x-ray photon energies may be established by exposing the detector to a practical range of photon energies. The same radiation dose may be delivered to the detector for this range of energies and the response of the detector for each energy may be determined.

The position (location) of the isotope source in three dimensions (3D) may be determined from the acquired image.

The image may then be post processed after acquisition to determine the source position.

The region of high intensity in the image is related to the location of the source. There are several ways in which points of high intensity may be determined, and for best accuracy, should take into account the need to remove the influence of statistical noise in the image arising from detector quantum efficiency.

One method of determining source position is Single Centre Profile Distribution Analysis. This method may be used to determine the source position parallel to the plane of the imager (X,Y).

The pixel that contains the maximum value is located and used as a starting point for processing. The maximum value pixel may be determined either by (i) a linear search or (ii) a scanned window approach. Method (i) provides faster processing speed, while method (ii) reduces the influence of statistical variations in pixel values due to random fluctuations in detected radiation known commonly as quantum noise.

Two orthogonal profiles may be obtained through this starting pixel point, in the horizontal and vertical direction (orthogonal). Both profiles may be filtered with a smoothing filter (5×1 pixel median convolution process) to reduce the influence of statistical variation between pixels. The maximum and minimum pixel value of each profile may be determined. The 80 percent value of the maximum (peak) value in each profile may also be determined. The process is not fixed to using 80% of peak. The mid position of the 80 percent width of the distribution may be calculated for each horizontal and vertical (orthogonal) profile. This gives the source position (x and y coordinates) in units of pixel position, and may be calculated to a sub-pixel resolution.

The x and y source position values may then be converted to units of millimetres by using the pixel pitch and dimension factors.

Another method is Multiple Centre Profile Distribution Analysis in which the position of the source may be determined by processing the distribution of the exposed circular exposure. The pixel that contains the maximum value may be located and used as a starting point for processing. Vertical profiles relative to the acquired image may be obtained through the exposed region, one through the location of the starting pixel position, then 10 profiles either side of the initial vertical profile. Horizontal profiles may also be obtained using the same starting pixel position, with 10 profiles either side of the initial horizontal position. Variations on the number of profiles used may be made to improve processing speed or to improve source position statistical accuracy. All profiles may be filtered with a smoothing filter (for example: 5×1 pixel median convolution process) to reduce the influence of statistical variation between pixels. The maximum and minimum pixel value of each profile may be determined. The 80 percent value of the maximum (peak) value in each profile may also be determined. The process is not fixed to using 80% of peak value. The mid position of the 80 percent width of the distribution may be calculated for all horizontal and vertical (orthogonal) profiles. The average value of the mid 80% position for all horizontal profiles may be calculated, to determine the sub pixel location of the source in the image x axis. The average value of the mid 80% position for all vertical profile may be calculated, to determine the sub pixel position of the source in the image y axis. The x and y source position values may then be converted to units of millimetres by using the pixel pitch and dimension factors.

Another method is Elliptical Fitting of Percentage Maximum Value in which the position of the source may be determined by processing the distribution of the exposed circular exposure. The pixel that contains the maximum value may be located and used as a starting point for processing. Vertical profiles relative to the acquired image may be obtained through the exposed region, one through the location of the starting pixel position, then 10 profiles either side of the initial vertical profile. Horizontal profiles may also be obtained using the same starting pixel position, with 10 profiles either side of the initial horizontal position. Variations on the number of profiles used may be made to improve processing speed or to improve source position statistical accuracy. All profiles may be filtered with a smoothing filter (for example: 5×1 pixel median convolution process) to reduce the influence of statistical variation between pixels. The average maximum pixel value of all profiles may be determined. The 60 percent value of the average maximum pixel value may also be determined. The process is not fixed to using an 60% of peak value. The 60% iso-pixel curve surrounding the central maximum of the exposed distribution may be determined. The four intersection points that intersect the 60% iso-pixel curve and the orthogonal lines the profiles were taken along may then be used to define an ellipse. Alternatively, the iso-pixel curve pixel points are used as data points for a regression fit of an elliptical function.

The centre point of the ellipse defines the sub pixel position of the source. The x and y source position values may then be converted to units of millimetres by using the pixel pitch and dimension factors.

As mentioned above the present invention also allows a determination of source distance from the imager (Z). A series of images may be acquired to establish a calibration function that relates acquired image characteristics to the known source distance from the imager. An image may be acquired for each source distance from the imager, over a clinically relevant range e.g. 20 mm to 300 mm, where 300 is the maximum distance the source is expected to be from the imager during experimental (clinical) data acquisition. The source may be held in a single catheter that is sandwiched between slabs of water equivalent phantom. The distance between the source and the imager may be increased by adding slabs of water equivalent phantom (10 mm intervals).

Source Distance Calibration may be performed using an Average Profile Width. In one embodiment orthogonal profiles through the exposed region are obtained using the method detailed above regarding single centre profile distribution analysis for each source to imager distance. The average of the 80% width distance (in units of pixels) for all profiles may be calculated. A polynomial function may be fitted to the distance vs average 80% width data to establish a source distance calibration function. Other functions can be fitted to the data to achieve a calibration function.

Another Method is to use Source Distance Calibration—Area of Region enclosed by a Percentage Maximum Value. The pixel that contains the maximum value may be located and used as a starting point for processing. Two orthogonal profiles may be obtained at through this starting pixel. Both profiles may be filtered with a smoothing filter (for example 5×1 pixel median convolution process) to reduce the influence of statistical variation between pixels. The average of the maximum value in the resulting smoothed profiles may be determined, which is known as the calculated maximum. For each acquired calibration image, the number of pixels which are included in the region enclosed by the 80% of calculated maximum value may be counted. A polynomial function may be fitted to the distance vs pixel count data to establish a source distance calibration function. Other functions may be fitted to the data to achieve a calibration function.

Yet another method is Source Distance Calibration—Length of Region border defined by a Percentage Maximum. The pixel that contains the maximum value is located and used as a starting point for processing. Two orthogonal profiles may be obtained at through this starting pixel (horizontal and vertical). Both profiles may be filtered with a smoothing filter (for example 5×1 pixel median convolution process) to reduce the influence of statistical variation between pixels. The average of the maximum value in the resulting smoothed profiles may be determined, which is known as the calculated maximum. For each acquired calibration image, the number of pixels which are included along the line encompassing the region enclosed by the 80% of calculated maximum value may be counted. A polynomial function may be fitted to the distance vs pixel count data to establish a source distance calibration function. Other functions may be fitted to the data to achieve a calibration function.

Another suitable method is Source Distance Calibration—Curvature of Profile Characterisation. The source generates a quasi-spherical fluence distribution which intersects with the planar imager to produce a distribution in the output image which may be considered as a curved surface in 3-dimensional space. The shape or curvature of this distribution depends upon the source-detector distance. An analytical function may be fitted by regression, or other optimisation technique, to the 3-D surface or to 1-dimensional profiles through the distribution, such that the fitting parameter(s) of the function characterise the curvature and may be shown to be related to the source-detector distance. There are a variety of mathematical functions which may be used for fitting, as it is actually not required that the fitted function closely match the distribution or profile. It is only necessary that the fit optimisation process converges to one or more fitting parameters that can be related unambiguously to the source-detector separation.

Examples of Suitable Functions:
Gaussian:

$$y = \frac{1}{s\sqrt{2\pi}} \exp\left[\frac{(x-x_0)^2}{2s^2}\right]$$

$x_0$ is the coordinate of the local maximum; s is the characteristic fitting parameter.

Lorentzian:

$$y = \frac{2A}{w} \frac{w}{4(x-x_0)^2 + w^2}$$

$x_0$ is the coordinate of the local maximum; A is the peak Area; w is the characteristic fitting parameter.

The local maximum pixel may be located as above and used as a starting point. Two orthogonal profiles may be obtained through this starting pixel. The profiles may be filtered with a smoothing filter (e.g. 5×1 pixel median convolution process) to reduce the influence of statistical variation between pixels. The fitting domain may be defined by the range of pixels around the local maximum which have an intensity above say 10% of the local maximum value. A regression function is fitted by minimising a cost function (e.g. sum of squares of differences between pixel values and fitted function calculated values at corresponding positions) over the fitting domain. Based on the teaching herein a skilled person may select a suitable fitting process. The resulting fitting parameter of interest may be compared against a calibration which has been previously established from a set of known geometries.

According to the dose calibration provided by the invention the image density (pixel value) to dose rate calibration may be achieved by exposing the imager to a range of source dose rates.

Due to the energy shift (x-ray spectrum change) that occurs when the isotope "beam" passes through solid water and a patient or subject, the calibration method must occur to be sensitive to this change. A change in x-ray spectrum, will change the imager response, as determined by the energy dependence of the imager (see FIG. 4 and the discussion on non-linear response to energy above.

The calibration method may require a calibrated detector for imager dose calibration. The detector may be exposed to the source in the equivalent manner to the exposure of the imager, e.g. by substitution, replication or by symmetrical arrangement. A phantom of water or other materials intended to approximate water or human tissue may be used. The detector response measured may be associated with the dose rate known by independent means e.g. i) direct measurement with another calibrated dosimeter, ii) analytical calculation—treatment planning system (TPS), iii) statistical calculation—Monte Carlo radiation transport modelling.

Measurements may be repeated for different source activities to isolate the influence of dose rate and spectrum, either by using different activity sources or time dependent decay if a single source.

The x and y source position of each image may be found using the multiple profile centre distribution analysis described above.

The response of the imager may be determined by calculating the average pixel value for a region of interest (ROI) of one or more pixels surrounding the calculated source position for each image.

A function may be fitted to measure and/or calculate dose rate responses and used to interpolate response as a function of dose rate.

A dose rate response function may be determined for each of a discrete set of distances, and a distance dependent dose rate function is derived. This may be represented either as an analytical function or as a lookup table. This may then be used as a calibration function for the imager accounting for dose rate, distance and energy spectrum dependence, where the distance is the ray path distance from the source to any pixel on the imager.

The implementation of HDR brachytherapy in vivo verification (source position and or dose distribution) may require the imager to be placed in the vicinity of the patient. Each component of the scenario (patient, imager and implant) has their own frame of reference. Implementation may occur with no geometric relationship, or with one or more relationships between the components.

There may be i) no relationship, ii) relationship between the implant and the imager, or iii) relationship between the patient, implant and imager.

The implant refers to a single brachytherapy catheter, multiple catheters, a brachytherapy applicator or a combination of catheters and applicators.

The patient may be a human subject or other life forms such as companion animals, performance animals and/or pets. The patient comprises the anatomical distribution about the implant.

The imager may be used to record the source position and dose distribution.

When there is no Geometric Relationship, in the simplest form, with no geometric relationship defined, the collection of measured source dwell positions, as a 3-D distribution, may be compared to the TPS planned dwell positions. This may be with no reference to absolute transfer tube/catheter/applicator position.

When there is a geometric relationship between the implant and imager, to verify the delivered dose (source position and dose distribution) relative to the implant, a geometrical relationship between the imager and the implant may be required. A process to determine the orientation of the implant relative to the imager is used.

Method 1a: External Radiation Source

The patient is prepared for HDR brachytherapy treatment delivery. X-ray marker devices are inserted into each catheter/applicator channel. The verification imager is located in a position that will be used during the treatment delivery. The imager acquires images of the implant using an external x-ray unit positioned beyond the patient. These images may then be used to calculate the position (in 3-D) of the implant/catheters relative to the imager. The treatment is delivered and source positions are recorded by the imager. The recorded source positions may then be referenced to the catheter positions and confirmation with the TPS is achieved. To verify the delivered dose (source position and dose distribution) relative to the patient, a geometrical relationship between the imager and the patient is required.

A process to determine the anatomical distribution relative to the imager may be used.

Method 1b: External Radiation Source and Implanted Fiducial Markers

The patient is prepared for HDR brachytherapy treatment delivery. X-ray marker devices are inserted into each catheter/applicator channel. The verification imager is located in a position that will be used during the treatment delivery. The patient has implanted fiducial markers implanted in the vicinity of the treatment volume/applicator. The fiducial markers are a representation of the position of the patient's soft tissue anatomy. The imager acquires images of the implant using an external x-ray unit positioned beyond the patient. These images may then be used to calculate the position (in 3-D) of the implant/catheters relative to the imager. These images also allow the position of the fiducial markers to be determined relative to the location of the implant/catheters. The treatment may be delivered and source positions may be recorded by the imager. The recorded source positions may then be referenced to the catheter positions and confirmation with the TPS is achieved.

The invention also provides treatment verification.

In Geometric Verification—Delivered source positions compared to TPS, the verification of treatment delivery may occur in a simple process whereby the recorded source dwell positions are compared to the planned dwell positions. This verification does not take into account the length of time the source dwelled at each position and is therefore not a dose verification method, but a source position verification.

Method 1c: Comparison of Source Positions for Single Catheter

All dwell positions in a given catheter are measured and determined relative to one reference dwell position or another reference point such as the catheter tip. Coordinates of dwell positions are determined using the methods described previously. The set of points in 3-D space may be registered against those planned, by employing standard registration techniques based on a minimised cost function. Based on the teachings herein a skilled person may readily select a suitable procedure of co-registration. Differences between each pair of planned and measured dwell positions remaining after co-registration may be reported.

Advantageously, this method enables real-time comparison against a treatment plan and facilitates error trapping and accident prevention due to errors in delivery of treatment or equipment malfunctions. Overdose prevention is made possible either by error notification to the operator for manual intervention, or by a direct treatment interrupt control signal to the afterloader, triggered by a pre-defined action level related to detected dwell position differences.

Method 2: Comparison of Source Positions for Total Brachytherapy Implant

The procedure described in Method 1 for a single catheter is repeated for all catheters in the entire implant. The dwell positions for all catheters are combined, and registered with the treatment plan as a complete implant set. Differences between corresponding planned and measured dwell positions are reported.

Method 3: Comparison of Source Positions Relative to Recorded Catheter and Implant Position and Orientation With an independent confirmation of the location and orientation of the implant (all needles/catheters), the relationship between the measured dwell positions (determined as per Method 2 above) and the implant is determined. For example, the spatial coordinates of the needle/catheter tips can be determined using an external x-ray imaging source employed in a classical stereo-shift tomography projection technique. That is, projection images obtained using the imaging panel, taken from different source positions, can identify the needle tip locations by triangulation.

In cases where there are a large number of catheters, each catheter may be uniquely identifiable in all projection images by inserting radio-opaque marker wires featuring a unique 'signature' of high and low density line segments and separations. These coordinates may be compared directly to the measured coordinates of the first dwell position of each catheter to confirm the tip offset. This gives a confirmation of the entire dwell position array relative to the implant, and allows quantitative description of any difference detected.

The invention also provides Dosimetric Verification—2D dose comparison between measured image and TPS predicted This verification of treatment delivery may be achieved by measuring the delivered dose at a plane (2-D face of the imager) and comparing this 2-D dose image with one predicted (calculated) by the treatment planning system (TPS). The geometric relationship between the imager and the implant, known via the image processing method described above, may be used to register the two images for comparison.

Any suitable techniques for comparison of the two dose distributions may be used. Based on the teachings herein a skilled person may select a suitable technique for making the comparison. Examples of suitable comparisons include the following.

(A) direct comparison of 1-dimensional profiles taken across the 2-dimensional dose distributions at corresponding spatial locations;

(B) 2-D dose distribution comparison by image subtraction. A 'difference map' may be produced by subtracting one from the other after normalisation (C) 2-D dose distribution comparison by gamma analysis. This comparison may be performed for entire image or a subset such as, a region of interest. Gamma analysis incorporating both pointwise difference and 'distance to agreement' may be utilized when comparing dose distributions.

(D) 2-D dose distribution comparison by histogram analysis. Dose per pixel frequency histograms may be generated for both distributions and compared.

The inventor's have also provided Treatment Analysis—3D dose calculation from measured source dwell positions.

An analysis of the treatment fraction of entire delivery may be achieved by using the measured source dwell positions as locations for an analytical dose calculation (such as may be performed using the TPS). The measured time the source dwelled at each position (derived from the afterloader signal or from imager acquisition) may then e used to calculate the dose delivered from each measured dwell position. A 3-D dose distribution of the treatment actually delivered may thereby be calculated. This distribution can then be compared to the original planned dose distribution.

The measured 3-D dose distribution may also be reconstructed over the original planning CT. The dose volume histograms (DVHs) can then be recalculated with the measured dose. The DVH indices may then be compared to the initial TPS predicted values.

In this way the present invention allows for the modification of all subsequent treatment fractions to achieve the initial desired total treatment dose distribution.

Verification may also be by dose back projection into patient volume. The 2-D dose distribution acquired by the 2-D detector may be back projected into the treatment volume. This may be done by projecting a rayline from each pixel in the dose image to the determined (from methods above) source position. A dose reconstruction plane may be established within the treated volume. The dose at each point on this plane may then be determined by correcting each initial rayline dose value by attenuation, inverse square law and photon scatter. Multiple dose reconstruction planes may be created to achieve a 3-D back projected dose distribution.

The invention also provides for clinical integration with an afterloader system. Treatment may be interrupted when some clinical threshold is reached that represents a potential detriment to the patient or significant deviation from the planned delivery of treatment. The interruption may be implemented by an output from the verification system connected to the safety stop and the source retract input lines of the afterloader.

The image acquisition, readout and store may be triggered by afterloader source control and source motion signals or by an independent system. Dwell step timing data may be captured directly from an afterloader source control and source motion signalling system where high resolution timing is required for shorter dwells. In one embodiment, the line out signals: 'source step' and 'radiation on' are accessed via a break-out box interface to provide the above functionality.

The following non-limiting examples illustrate the invention. These examples should not be construed as limiting: the examples are included for the purposes of illustration only. The Examples will be understood to represent an exemplification of the invention.

EXAMPLES

The EPID used throughout all experiments was an amorphous silicon flat panel imager (Varian Medical Systems, Palo Alto, Calif.), detector model IAS11-19 running software version 6.1.11. Normally fitted to an external beam linear accelerator, the detector was removed and remained mobile for all measurements. The imager is operated using the AM Maintenance software module (version 7.1.2003.905). The EPID has a 400×300 mm$^2$ detection area (512×384 pixels), a 1 mm Cu build-up layer, a phosphor screen and a hydrogenated a-Si:H photodiode array. The touch guard cover was removed for all measurements. Further details regarding similar types of imagers can be found in an overview by Antonuk et al.[18]

The stored EPID image is the average of all frames captured between the start and stop signals that define an image acquisition. Each frame is defined as the signal from one readout of the entire photodiode array. This average of all frames, makes the interpretation of EPID output, as dose, complex. Due to the limited size of the image frame buffer, the system is required to transfer data out of the image frame buffer every 64 frames. The data transfer does not interrupt the accumulation of charge in the photodiode array, but adds a readout delay for the next frame of ~0.164 s. The result is an extended acquisition time for the frame following every 64$^{th}$ frame acquired[19]. The EPID Signal ($S_{EPID}$) is defined as the average pixel value for a region of interest in the stored EPID image. The EPID signal is a representation of dose rate seen at the EPID detection plane. In this work, we define the response of the EPID as the EPID signal. The EPID response represents average dose rate over the image acquisition interval. Note, this is different to EBRT case where long beam on intervals allow EPID signal multiplied by time to be used as a surrogate for integrated dose.

$$R_{EPID} = S_{EPID} \quad (1)$$

The time parameter is not included in the definition of response because, in this application, where exposures times can be small due to very short source dwell times, the time resolution of the image acquisition is poor. The integral dose can be calculated by applying a dose rate conversion function (DRCF) and a time value to the EPID response.

$$\text{Dose} = \text{DRCF} \times R_{EPID} \times T \quad (2)$$

The time value T is the EPID image acquisition time or the high resolution time derived from the afterloader drive signals.

All stored EPID images were acquired using the service monitor module in the AM Maintenance software. Image correction for each acquired image Iraw—Idark/Iflood. Flood field correction was set identically to one, as the overall variation in pixel sensitivity was found to be insignificant.

Phantom and Measurement Setup

Figure 2:
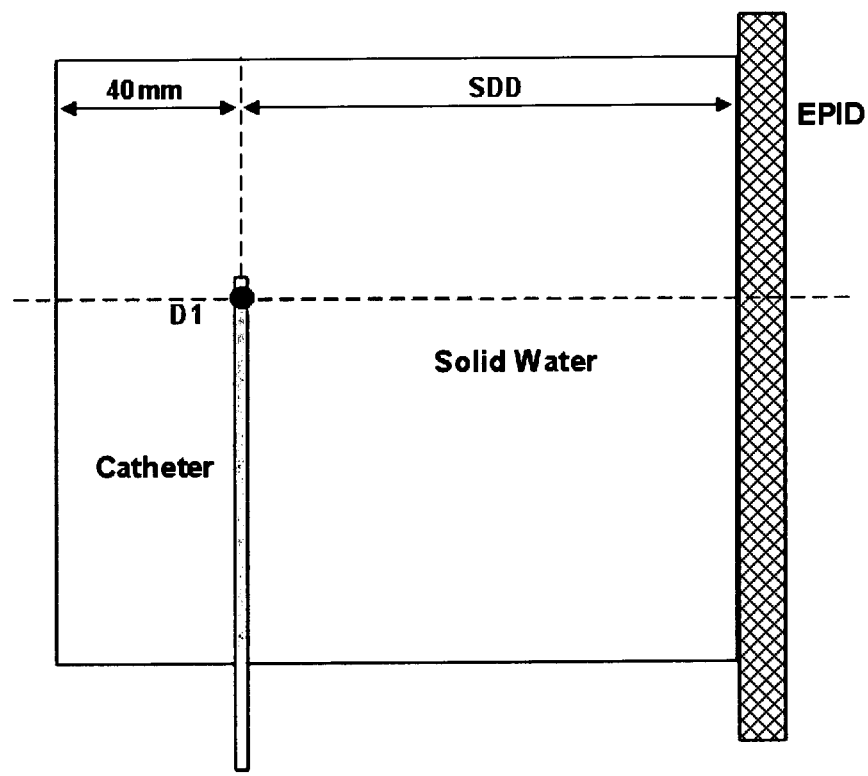
FIG. 2: The solid water phantom setup for measurements with the EPID. The brachytherapy catheter was placed between slabs of solid water. The brachytherapy source was driven through the catheter and stopped at a dwell position (D1). Measurements were made at different SDDs by removing or adding solid water slabs between the catheter and the EPID.

A phantom was created from 15 slabs of polymethylmethacrylate (PMMA), also known as solid water (300×300×150 mm). A brachytherapy plastic interstitial catheter (ProGuide 6F, Nucletron), containing the Ir192 source, was inserted between the slabs. The phantom was placed against the detection side of the EPID, which was positioned vertically. There was no gap between the EPID surface and the 300×300 mm phantom surface, and both were parallel to the catheter. The distance from the catheter to the EPID surface could be varied by changing the number of solid water slabs between them. A schematic diagram of the phantom, source and EPID is shown in FIG. 2.

All HDR brachytherapy measurements were made by driving the source to the desired dwell position before image acquisition was started, which eliminated any contribution of source transit dose to the measured data. Repeat images were acquired for each measurement, to avoid observed EPID response build up effects. Sufficient time between successive measurements was allowed to eliminate any ghosting contributions. This can also be achieved by using reset frames (which are discarded) to dissipate residual charge from the photodiode array. Background images were acquired without radiation to ensure a zero response from the EPID before data acquisition. The effects of response build up and ghosting for HDR brachytherapy measurements will be examined in future work.

EPID Response to Energy

To the authors' knowledge, the use of an EPID for HDR brachytherapy dosimetry has never been reported. To determine the energy response of the EPID over a range of x-ray energies, including the kilo-voltage range of the Ir192 source, the EPID was exposed to a range of x-ray sources using facilities at the ionising radiation standards laboratory, Australian Radiation Protection and Nuclear Safety Agency (ARPANSA). The EPID was setup on the 'SEIFERT' orthovoltage x-ray system (Isovolt 450/9, Rich. Seifert & Co) which produces ISO 4037 standard 'narrow' series x-ray beams[20] using a constant potential tungsten target x-ray tube. These 'narrow' beams are highly filtered (hardened) to produce a narrow x-ray energy spectrum. The resulting dose rates are low, due to the high filtration of these beams, on the order of 5 μGy/s at 1 m from the source. The EPID was set at 1 m from the x-ray source and 0.5, 1, 2 and 3 mGy was delivered to the EPID at energies from 60 to 300 kVp (Effective energy of 48 to 251 keV), giving an exposed circular area of approximately 10 cm in diameter.

A customised x-ray beam on the SIEFERT system was established to mimic the energy of the major peak in the Ir192 spectrum[21], which peaks at 317.5 keV and contains 49% of the photon flux. The peak energy of the customised x-ray beam was 400 keV with a beam filtration of 6.6 mm Pb+2 mm Sn+4 mm Al, to produce an effective x-ray energy of 317.5 keV.

With the use of a reference transmission chamber, accurate dose rates were able to be specified at the EPID surface. An air kerma rate of 5 μGy/s at the EPID surface was used for all measurements with the ISO narrow beam series. Four doses; 0.5, 1.0, 2.0 and 3.0 mGy, were delivered to the EPID, at 5 μGy/s, for each of the x-ray energies in the ISO narrow beam series. These four doses were also delivered to the EPID using the Co60 (1.2 MeV) and Cs137 (662 keV) systems available at ARPANSA.

The EPID was exposed to the Ir192 HDR brachytherapy source at the William Buckland Radiotherapy Centre (WBRC) and the same four doses were delivered to the EPID.

EPID Response to Dose Rate

Determining the dose rate response of the EPID, with the Ir192 brachytherapy source, required a change of dose rate at the EPID surface. The phantom was setup with a SSD of 100 mm, the source driven to dwell position D1, and an image acquired with an acquisition time 11.934 seconds (100 frames). This measurement was then repeated over the clinical life of the source, approximately 3 months, in which the source decayed from approximately 10 Ci to approximately 4 Ci.

Reproducibility

The reproducibility of the EPID response was determined by evaluating repeated measurements taken for the dose rate response measurement above. The Ir192 source air kerma rate (AKR) decreased from 3.866 cGy/h/m$^2$ to 1.694 cGy/h/m$^2$ over the period the measurements were taken. Each measurement was then corrected for the source decay to a AKR of 4.082 cGy/h/m$^2$ (10 Ci), which is a commonly used reference activity value in HDR brachytherapy.

EPID Source Position Resolution and Accuracy

The accuracy of the EPID to determine the Ir192 brachytherapy source position in a plane parallel to the EPID was investigated. The phantom was set up with a SDD of 30 mm and the source was driven to 11 dwell positions (10 source steps), with a source step size of 10 mm. An image was acquired at each source dwell position. The 11 dwell positions were then repeated for step sizes of 5.0 mm and 2.5 mm, with images acquired at each dwell position. The measurement process was then repeated for a SDD of 100 mm.

The source position accuracy in the depth plane was then determined by acquiring images of the source at varying SDDs (depths). Images were acquired for a single source position at a range of depths from 10 mm to 100 mm. These images were then analysed and the depth resolution determined EPID Calibration The calibration of the EPID for two dimensional dose rate measurements requires a dose rate conversion function, which converts the measured EPID response to a dose rate value. The function is not a linear function of applied dose rate, but is also a function of pixel distance to the source for each pixel in the EPID image. The increased path length from the source to each pixel in the image, needs to be accounted for, and so a dose rate calibration at various SDDs is required to calibrate the EPID for dose rate measurements.

To achieve a dose rate calibration, EPID images were acquired for SDDs of 10 mm to 100 mm. The dose rate at these SDDs was then calculated and the gradient of each SDD response determined (Response/Dose Rate). Each response gradient was then plotted against the SDD they were acquired at to determine a plot of the dose rate calibration function as a function of depth.

EPID Dose Rate Calibration Verification

To verify the dose rate calibration function was acceptable, the source was driven to position D1, at a depth of 30 mm. An image was acquired and the raw image data compared to data from the TPS. The dose rate calibration function was then applied to the measured image and then compared to the TPS.

Proof of Principle Measurement

To test the concept of EPID dosimetry for HDR brachytherapy, the source was driven to an arbitrary position in the catheter, at an arbitrary depth. The position of the source was determined as well as the dose rate from the measured EPID image using the EPID calibration functions determined previously. These values were then compared to the known source position and the planning dose rate data from the TPS.

Simple Plan Measurement

Figure 3:
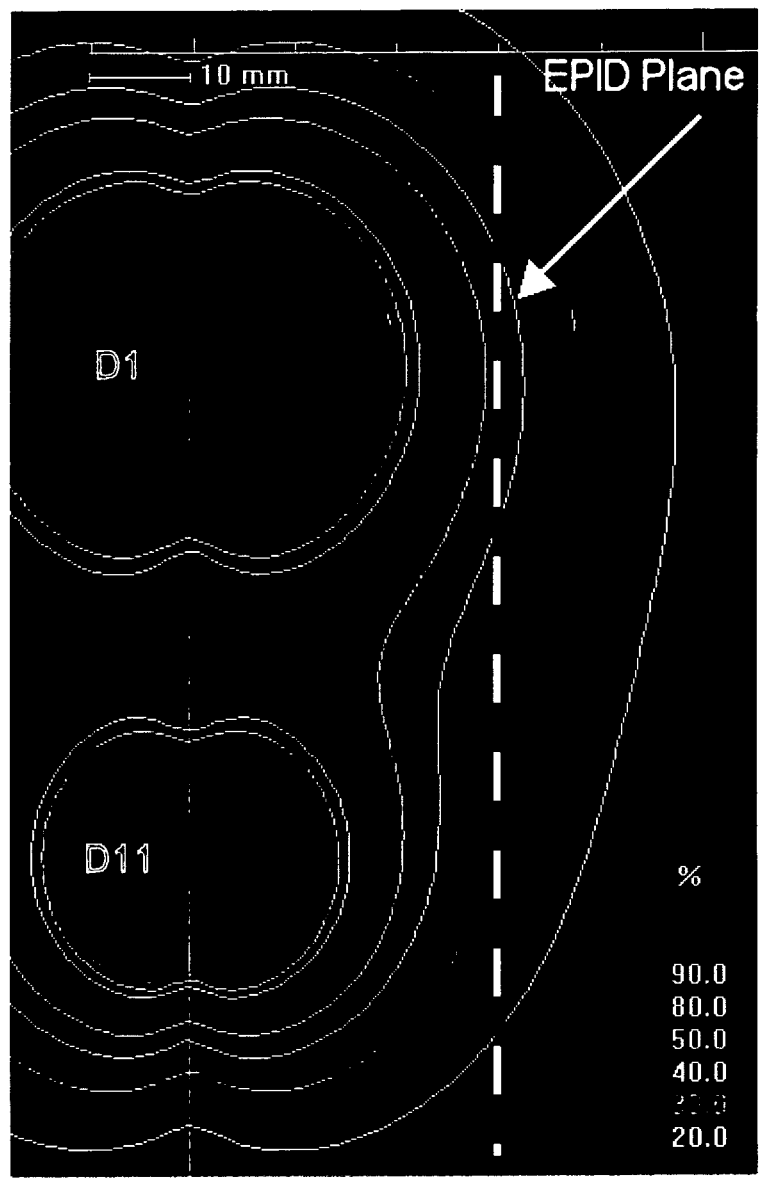
FIG. 3: The isodoses for a sample treatment plan created to test the dose verification method. The plane of the EPID is shown as dashed line, 30 mm from the catheter. The sample plan consists of 2 source dwell positions, D1 and D11, 50 mm apart, with a dwell time weighting of 1.0 and 0.44.

A simple 'treatment plan' was created using two dwell positions (FIG. 3), separated by 50 mm. The aim was to produce a distribution that shows some modulation through the treatment volume that may be imaged by the EPID. The EPID was positioned 30 mm from the source, parallel to the catheter, orthogonal to the dashed (yellow) line in FIG. 3. The treatment plan delivered 50 cGy to the 100% isodose, with dwell weights of 1.00 and 0.44 for dwell positions D1 and D11. The A profile from the EPID measured dose in the was then compared to the equivalent profile from the TPS.

Results

EPID Response to Energy

Figure 4:
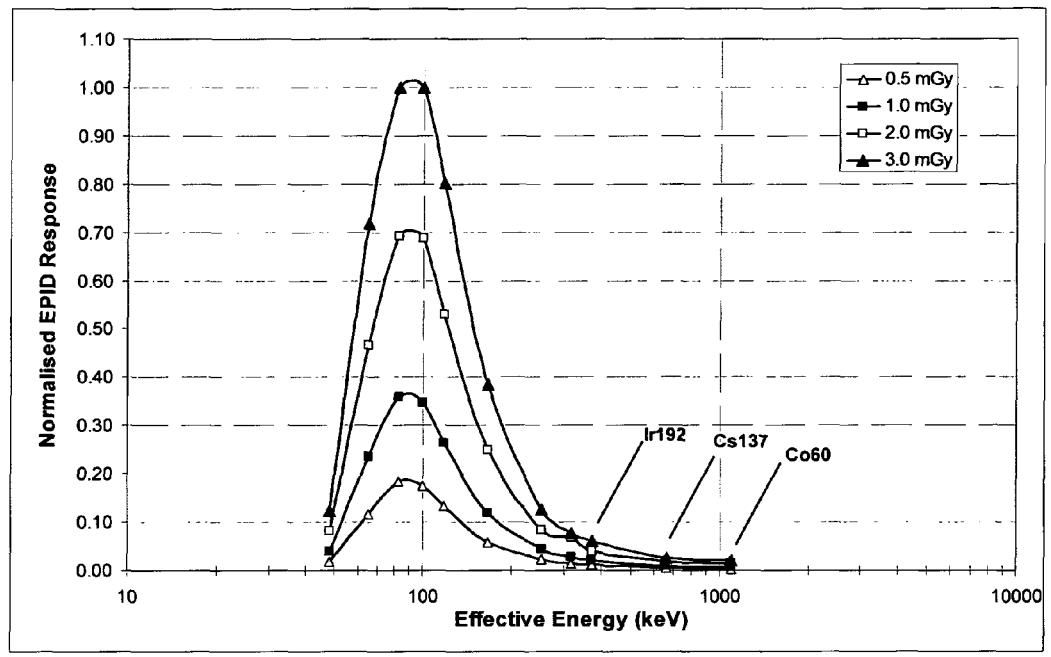
FIG. 4: The EPID energy response for a range of x-ray beams delivering 0.5 to 3.0 mGy. The data points for the 3 isotopes are identified for clarity.

The EPID shows a strong energy dependence to the incident x-rays below an effective energy of 250 keV, with a peak response at 90 keV (FIG. 4). Above this the EPID appears to be energy independent.

EPID Response to Dose Rate

Figure 5:
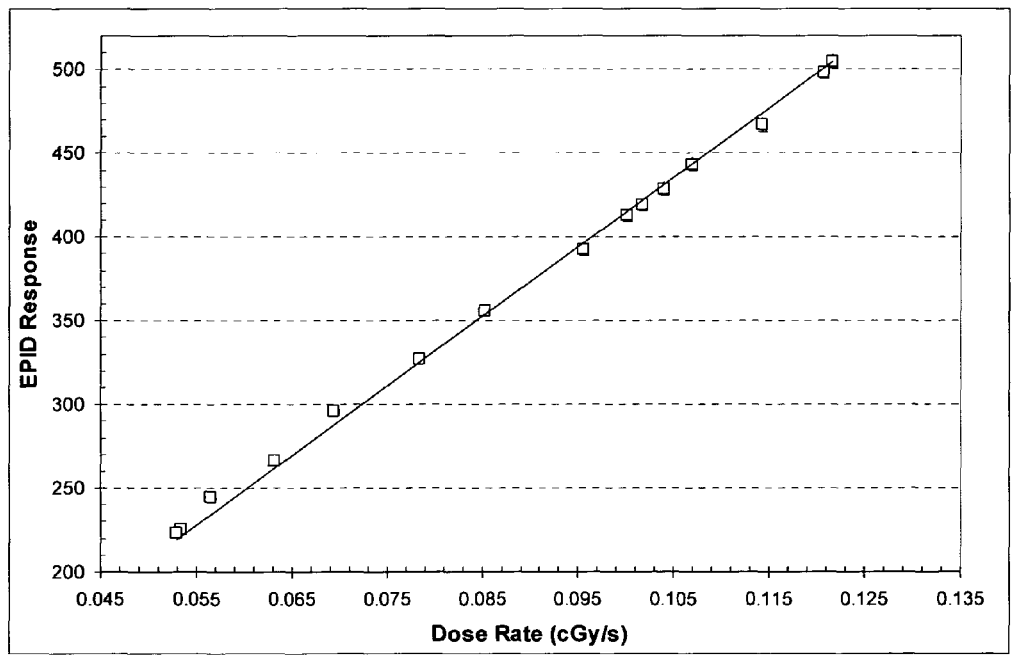
FIG. 5: The linear dose rate response of the EPID with the Ir92 source measured in a solid water phantom of FIG. 2, with a SDD of 100 mm.

The response of the EPID to dose rate is linear. FIG. 5 shows the dose rate response of the EPID over a 3 month period, with a reduction in activity from ~10 Ci to ~4 Ci. Error bars are shown at each measurement point, which represent +/−1 standard deviation of the ROI pixel values for all measurements taken at each point.

Reproducibility

Figure 6:
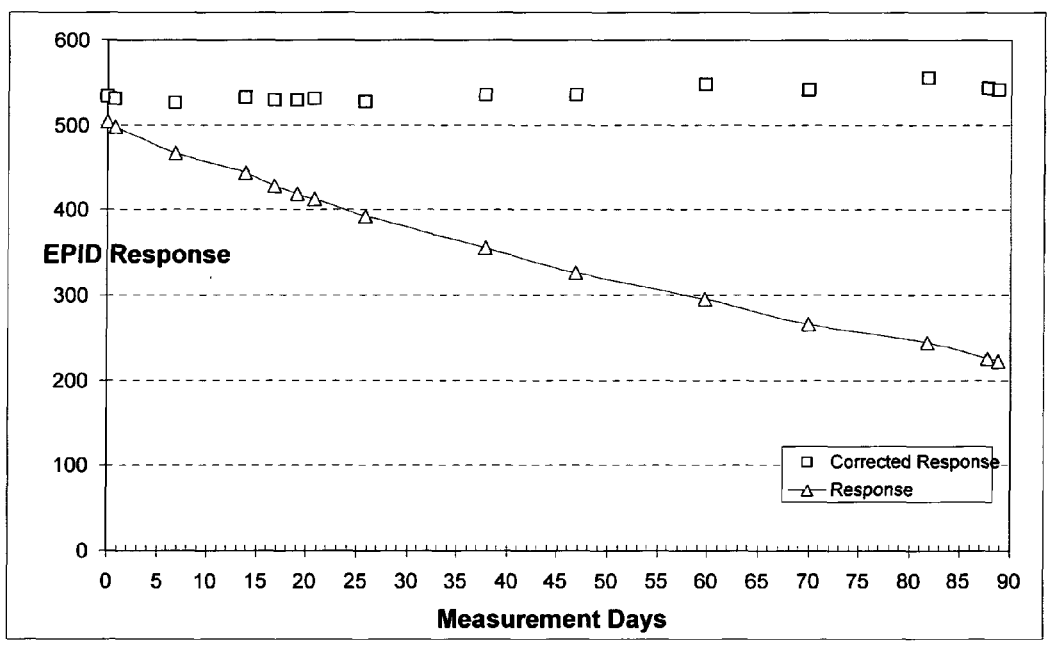
FIG. 6: The response measurement reproducibility of the EPID over the clinical life of the source, which is approximately 3 months. The EPID produces reproducible results to less than 2%.

FIG. 6 shows the response measurement reproducibility of the EPID over the clinical life of the source, which is approximately 3 months. The EPID produces reproducible results to less than 2%

Source Position Accuracy

Figure 7:
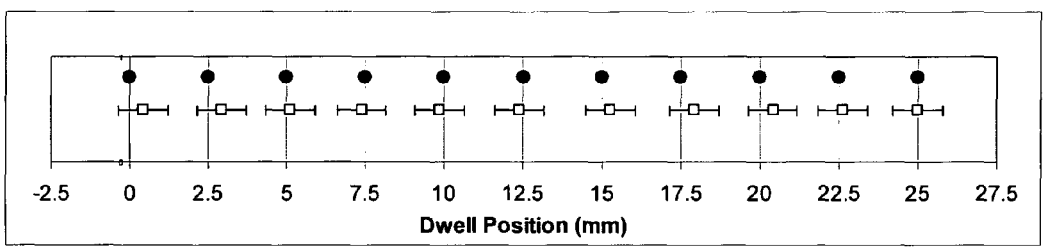
FIG. 7: The measured (square) and expected (disc) source positions for a step size of 2.5 mm at a SDD of 30 mm(a) and 100 mm(b). The 100 mm SDD with 2.5 mm step size is a worst case scenario, with smallest source step size at large EPID distance.
Figure 7:
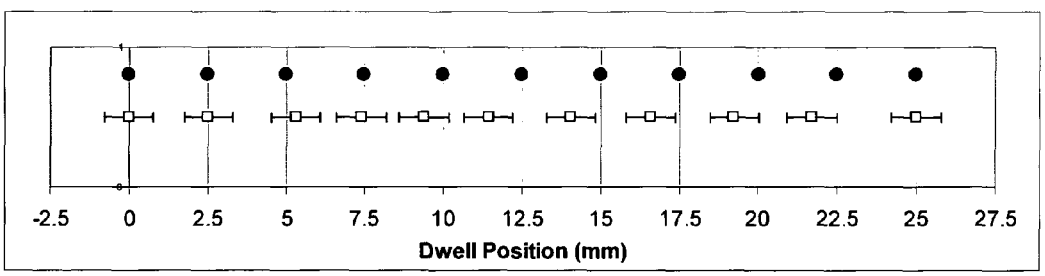

The precision of the source position parallel to the X-Y plane of the EPID was found to be always less than 1 pixel (0.784 mm) at a SDD of 30 mm, while at a SDD of 100 mm, the source position precision was always found to be less than 2 pixels. FIG. 7 below shows measured and expected source positions at the two SDDs for a source step size of 2.5 mm. The measurement of source dwell position shows excellent agreement with the known source dwell positions as verified by film placed in contact with the catheter distal to the EPID . . .

An example of SDD (z coordinate) determination is illustrated for images processed by calculating the width of the 80% value from the peak height of the image. The average value was taken for 10 profiles around the source position in the x any y direction across the peak. This "Peak Width Index" was then plotted against the depth measured at to achieve a source depth calibration function.

Figure 8:
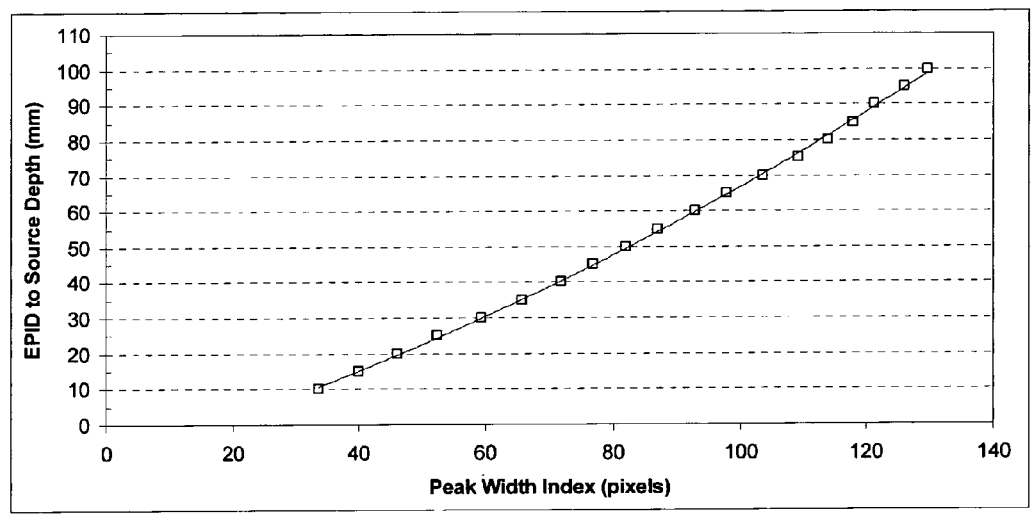
FIG. 8: The source depth calibration function showing a fitted polynomial to the data. The Peak Index is the mean width of profile at 80% of the maximum.

FIG. 8 shows the source depth calibration function showing a fitted polynomial to the data. The Peak Width Index is the mean width of profile at 80% of the maximum. This method was validated against two arbitrary geometries of SDD equal to 35 mm and 42 mm. The determined SDD using this method was 35.5±0.6 mm and 41.6±0.6 mm.

EPID Calibration

Unlike EPID dosimetry in external beam radiotherapy (EBRT), the geometric relationship between the radiation source, patient, and detector, influences the EPID response to dose rate. This is due to the significant differences in path length between source and detector elements and the consequential spectral changes due to differential attenuation and scattering. For this reason, a distance dependent calibration must be used.

Figure 9:
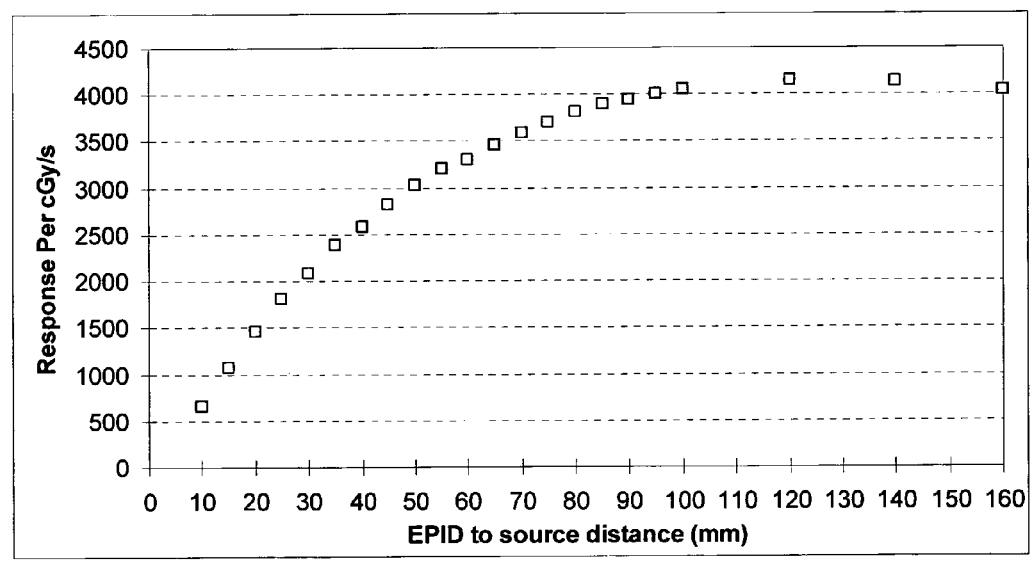
FIG. 9: The response per dose rate as function of distance from the measurement point to the source.

FIG. 9 shows the response per dose rate as function of distance from the measurement point to the source. It demonstrates the need for a distance dependant calibration curve to correct for photon spectral change, due to scattering and attenuation, and provides a means for implementing this.

EPID Dose Rate Calibration Verification

Figure 10:
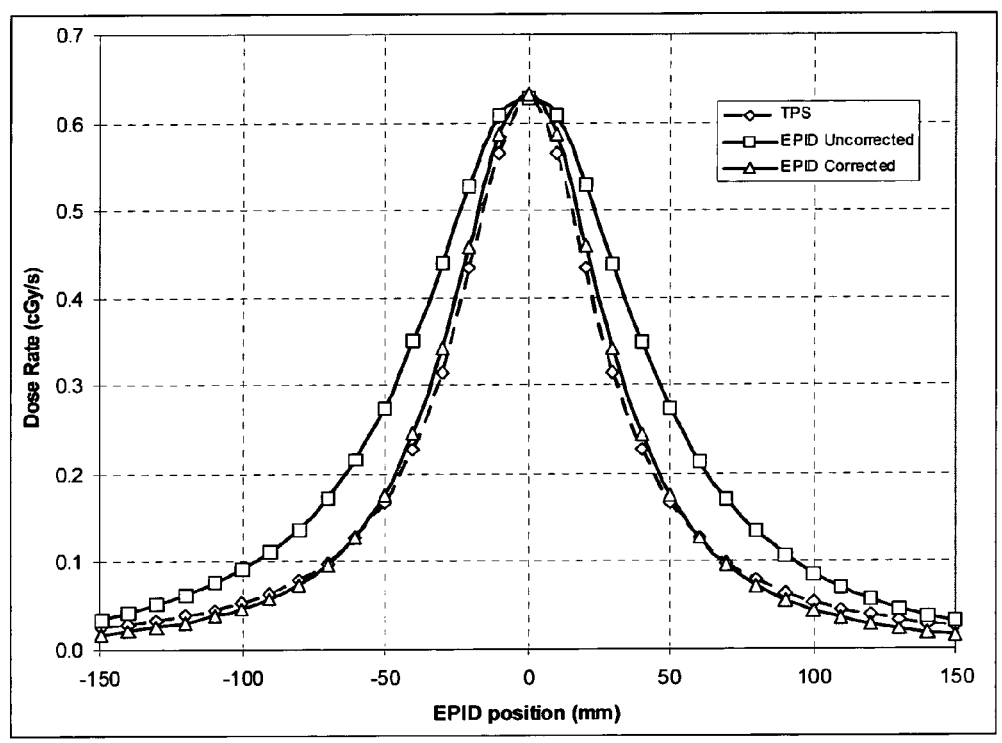
FIG. 10: TPS profile data, the measured EPID data without correcting for off axis measurement distance changes and the corrected EPID data.

The dose rate calibration function was verified by applying it to a single dwell measured at a SDD of 30 mm. FIG. 10 shows a profile from the TPS, together with a measured profile using our distance-dependent calibration function. Also shown is a profile using a simple first-order, distance independent calibration relationship. This illustrates the inherent error caused by not accounting for spectral changes and energy dependence of the detector response.

Simple Plan Measurement

The EPID images for the simple treatment plan of two dwell positions is shown in FIG. 11(a). The overlay crosshair represents the location of the first dwell position in the plan, D1, as determined by analysis of the image data. The image in FIG. 11(b) represents the dose plane exported from the TPS at the position of the EPID surface.

Figure 11:
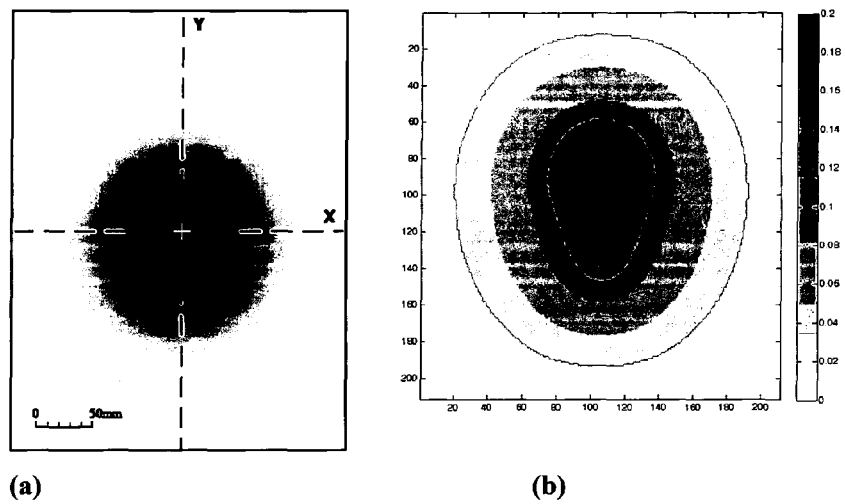
FIG. 11(a): The EPID image acquired at a SDD of 30 mm for the simple treatment plan. The cross hair represents the calculated position of the first source dwell position in the plan.
FIG. 11(b): The planned dose distribution at a plane of 30 mm from the catheter exported from the TPS. For visual comparison with the measured image, a cross hair has been added at source position 1.

FIG. 11 (a) The EPID image acquired at a SDD of 30 mm for the simple treatment plan. The cross hair represents the calculated position of the first source dwell position in the plan. 11(b) The planned dose distribution at a plane of 30 mm from the catheter exported from the TPS. For visual comparison with the measured image, a cross hair has been added at source position 1.

Figure 12:
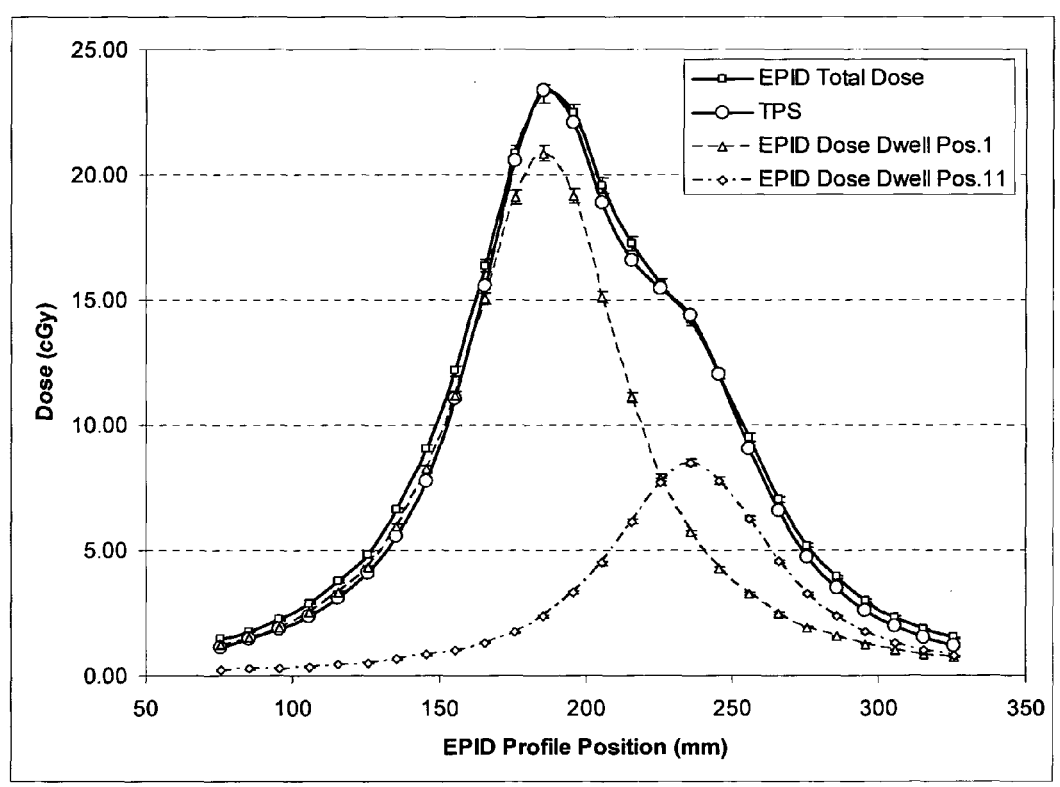
FIG. 12: shows a measured dose profile that has been reconstructed from the individually acquired single dwell image profiles (also shown) and the distance-dependent calibration function. The measured profile is overlayed with the TPS calculated expected profile, showing excellent agreement, and proves the principle.

FIG. 12 shows a measured dose profile that has been reconstructed from the individually acquired single dwell image profiles (also shown) and the distance-dependent calibration function. The measured profile is overlayed with the TPS calculated expected profile, showing excellent agreement, and proves the principle The inventors have developed a novel system for dosimetry of brachytherapy. The invention provides a check of both source positions and dwell times during dose delivery, something that is not currently available. The present inventors have made comprehensive real-time dosimetry of brachytherapy feasible beyond simple point dose verification using a 2D array detector. The images are sensitive enough to reveal clinically relevant source position and dwell time errors. The present inventors' contribution has the potential to eliminate previously unidentified treatment errors in brachytherapy, and improve quality control.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

1. P. J. Hoskin, P. J. Bownes, P. Ostler, K. Walker and L. Bryant, "High dose rate afterloading brachytherapy for prostate cancer: catheter and gland movement between fractions," Radiother Oncol 68, 285-288 (2003).

2. J. Valentin, "Prevention of high-dose-rate brachytherapy accidents. ICRP Publication 97," Ann ICRP 35, 1-51 (2005).

3. D. P. Dearnaley, M. R. Sydes, J. D. Graham, E. G. Aird, D. Bottomley, R. A. Cowan, R. A. Huddart, C. C. Jose, J. H. Matthews, J. Millar, A. R. Moore, R. C. Morgan, J. M. Russell, C. D. Scrase, R. J. Stephens, I. Syndikus and M. K. Parmar, "Escalated-dose versus standard-dose conformal radiotherapy in prostate cancer: first results from the MRC RT01 randomised controlled trial," Lancet Oncol 8, 475-487 (2007).

4. A. Pollack, G. K. Zagars, J. A. Antolak, D. A. Kuban and Rosen, II, "Prostate biopsy status and PSA nadir level as early surrogates for treatment failure: analysis of a prostate cancer randomized radiation dose escalation trial," Int J Radiat Oncol Biol Phys 54, 677-685 (2002).

5. R. Das, W. Toye, T. Kron, S. Williams and G. Duchesne, "Thermoluminescence dosimetry for in-vivo verification of high dose rate brachytherapy for prostate cancer," Australas Phys Eng Sci Med 30, 178-184 (2007).

6. Z. Y. Qi, X. W. Deng, S. M. Huang, J. Lu, M. Lerch, D. Cutajar and A. Rosenfeld, "Verification of the plan dosimetry for high dose rate brachytherapy using metal-oxide-semiconductor field effect transistor detectors," Med Phys 34, 2007-2013 (2007).

7. K. Tanderup, J. J. Christensen, J. Granfeldt and J. C. Lindegaard, "Geometric stability of intracavitary pulsed dose rate brachytherapy monitored by in vivo rectal dosimetry," Radiother Oncol 79, 87-93 (2006).

8. J. Lambert, T. Nakano, S. Law, J. Elsey, D. R. McKenzie and N. Suchowerska, "In vivo dosimeters for HDR brachytherapy: a comparison of a diamond detector, MOSFET, TLD, and scintillation detector," Med Phys 34, 1759-1765 (2007).

9. F. Lacroix, L. Archambault, L. Gingras, M. Guillot, A. S. Beddar and L. Beaulieu, "Clinical prototype of a plastic water-equivalent scintillating fiber dosimeter array for QA applications," Med Phys 35, 3682-3690 (2008).

10. J. Lambert, D. R. McKenzie, S. Law, J. Elsey and N. Suchowerska, "A plastic scintillation dosimeter for high dose rate brachytherapy," Phys Med Biol 51, 5505-5516 (2006).

11. I. A. Brezovich, J. Duan, P. N. Pareek, J. Fiveash and M. Ezekiel, "In vivo urethral dose measurements: a method to verify high dose rate prostate treatments," Med Phys 27, 2297-2301 (2000).

12. W. Toye, R. Das, T. Kron, R. Franich, P. Johnston and G. Duchesne, "An in vivo investigative protocol for HDR prostate brachytherapy using urethral and rectal thermoluminescence dosimetry," Radiother Oncol (2008).

13. G. Anagnostopoulos, D. Baltas, A. Geretschlaeger, T. Martin, P. Papagiannis, N. Tselis and N. Zamboglou, "In vivo thermoluminescence dosimetry dose verification of transperineal 192Ir high-dose-rate brachytherapy using CT-based planning for the treatment of prostate cancer," Int J Radiat Oncol Biol Phys 57, 1183-1191 (2003).

14. P. B. Greer and C. C. Popescu, "Dosimetric properties of an amorphous silicon electronic portal imaging device for verification of dynamic intensity modulated radiation therapy," Med Phys 30, 1618-1627 (2003).

15. E. E. Grein, R. Lee and K. Luchka, "An investigation of a new amorphous silicon electronic portal imaging device for transit dosimetry," Med Phys 29, 2262-2268 (2002).

16. B. M. McCurdy, K. Luchka and S. Pistorius, "Dosimetric investigation and portal dose image prediction using an amorphous silicon electronic portal imaging device," Med Phys 28, 911-924 (2001).

17. L. N. McDermott, R. J. Louwe, J. J. Sonke, M. B. van Herk and B. J. Mijnheer, "Dose-response and ghosting effects of an amorphous silicon electronic portal imaging device," Med Phys 31, 285-295 (2004).

18. L. E. Antonuk, "Electronic portal imaging devices: a review and historical perspective of contemporary technologies and research," Phys Med Biol 47, R31-65 (2002).

19. A. Van Esch, T. Depuydt and D. P. Huyskens, "The use of an aSi-based EPID for routine absolute dosimetric pre-treatment verification of dynamic IMRT fields," Radiother Oncol 71, 223-234 (2004).

20. I. O. f. Standardization., "X and gamma reference radiation for calibrating dosemeters and doserate meters and for determining their response as a function of photon energy-Part 1: Radiation characteristics and production method." in *ISO* 4037-1, (Geneva: ISO, 1996).

21. G. M. Daskalov, E. Loffler and J. F. Williamson, "Monte Carlo-aided dosimetry of a new high dose-rate brachytherapy source," Med Phys 25, 2200-2208 (1998).

22. C. Kirkby and R. Sloboda, "Consequences of the spectral response of an a-Si EPID and implications for dosimetric calibration," Med Phys 32, 2649-2658 (2005).

The invention claimed is:

1. A method for verifying a high dose rate brachytherapy radiation treatment including the steps of:
    processing a distribution of exposure to a high dose rate brachytherapy radiation source of a two dimensional electronic portal imaging array to determine a region of high exposure;
    obtaining one or more distribution of exposure profiles through the region of high exposure;
    determining a region of high value in the one or more distribution of exposure profiles; and
    calculating one or more high dose rate brachytherapy radiation source position and/or one or more high dose rate brachytherapy radiation source distance from the determined region of high exposure and/or high value to thereby verify at least a part of the high dose rate brachytherapy radiation treatment.

2. The method of claim 1 wherein the verification of the high dose rate brachytherapy radiation treatment is dose verification and/or source position verification.

3. The method of claim 1 wherein the distribution of exposure profile processed is for an elapsed time period of the high dose rate brachytherapy radiation treatment.

4. The method of claim 1 further including generating a report comprising the calculated one or more high dose rate brachytherapy radiation source positions and/or brachytherapy radiation source distances.

5. A system for verifying a high dose rate brachytherapy radiation treatment, the system comprising:
    an input for receiving a distribution of exposure to a high dose rate brachytherapy radiation source of a two dimensional electronic portal imaging array;
    a processor for determining a region of high exposure in the distribution of exposure;
    a processor for obtaining one or more distribution of exposure profiles through the region of high exposure;
    a processor for determining a region of high value in the one or more distribution of exposure profile; and
    a processor for calculating one or more high dose rate brachytherapy radiation source position and/or one or more high dose rate brachytherapy radiation source distance from the determined region of high value.

6. The system of claim 5 wherein the verification of the high dose rate brachytherapy radiation treatment is dose verification and/or source position verification.

7. The system of claim 5 further comprising a report generator for generating a report comprising the calculated one or more high dose rate brachytherapy radiation source positions and/or one or more high dose rate brachytherapy radiation source distances.

8. A non-transitory computer program product said computer program product comprising:
    a computer usable medium and computer readable program code embodied on said computer usable medium for verifying high dose rate brachytherapy radiation treatment, the computer readable code comprising:
    computer readable program code devices (i) configured to cause the computer to process a distribution of exposure to a high dose rate brachytherapy radiation source of a two dimensional electronic portal imaging array to determine a region of high exposure;
    computer readable program code devices (ii) configured to cause the computer to obtain one or more distribution of exposure profiles through the region of high exposure;
    computer readable program code devices (iii) configured to cause the computer to determine a region of high value in the one or more distribution of exposure profiles; and
    computer readable program code devices (iv) configured to cause the computer to use the determined region of high value to calculate one or more high dose rate brachytherapy radiation source position and/or one or more high dose rate brachytherapy radiation source distance to thereby verify at least a part of the brachytherapy radiation treatment.

9. A method for determining a high dose rate brachytherapy source distance from a two dimensional electronic portal imaging array including the steps of:
    processing a distribution of exposure to a high dose rate brachytherapy radiation source of the two dimensional electronic portal imaging array to determine a region of high exposure;
    determining a curvature parameter that describes or characterises the distribution of the exposure in the region of high exposure; and
    relating the curvature parameter to calibration data or to a function of the calibration data to thereby determine the high dose rate brachytherapy source distance from the two dimensional imaging array.

10. The method of claim 9 wherein the step of determining the curvature parameter may include:
    obtaining one or more distribution of exposure profiles through the region of high exposure; and
    determining an average width distance at a percentage of an average maximum value for the one or more distribution of exposure profiles.

11. A system for determining a high dose rate brachytherapy source distance from a two dimensional electronic portal imaging array comprising:
    a processor for processing a distribution of exposure to a high dose rate brachytherapy radiation source of the two dimensional electronic portal imaging array to determine a region of high exposure;
    a processor for determining a curvature parameter that describes or characterises the distribution of the exposure in the region of high exposure; and
    a processor for relating the curvature parameter to calibration data or to a function of the calibration data to thereby determine the high dose rate brachytherapy source distance from the two dimensional imaging array.

12. The system of claim 11 wherein the determination of the curvature parameter includes:
    obtaining one or more distribution of exposure profiles through the region of high exposure; and
    determining an average width distance at a percentage of an average maximum value for the one or more distribution of exposure profiles.

13. A non-transitory computer program product said computer program product comprising:
    a computer usable medium and computer readable program code embodied on said computer usable medium for determining a high dose rate brachytherapy source distance from a two dimensional electronic portal imaging array, the computer readable code comprising:

computer readable program code devices (i) configured to cause the computer to process a distribution of exposure to the high dose rate brachytherapy radiation source of the two dimensional electronic portal imaging array to determine a region of high exposure;

computer readable program code devices (ii) configured to cause the computer to determine a curvature parameter that describes or characterises the distribution of exposure in the region of high exposure; and computer readable program code devices (iii) configured to cause the computer to relate the curvature parameter to calibration data or to a function of the calibration data to thereby determine high dose rate the brachytherapy source distance from the two dimensional imaging array.

14. A method of calibrating a high dose rate brachytherapy radiation dosage including the steps of:

exposing a two dimensional electronic portal imaging array to a high dose rate brachytherapy radiation source to obtain a measured response;

associating the measured response of the imaging array to the high dose rate brachytherapy radiation source to a known dosage;

determining the high dose rate brachytherapy radiation source position using the method of claim 1;

determining a response of the imaging array by calculating an average pixel value for a region of interest of one or more pixels surrounding the determined source position;

fitting the determined response and/or the known dosage to calculate a dose rate response function for each distance in a set of high dose rate brachytherapy radiation source distances; and applying the calculated dose rate response function to the high dose rate brachytherapy radiation dosage detected by the imaging array to calibrate the detected high dose rate brachytherapy radiation dosage.

15. The method of claim 14 wherein the step of associating the measured response comprises direct measurement with another calibrated dosimeter and/or analytical calculation.

16. A system of calibrating a high dose rate brachytherapy radiation dosage comprising:

a two dimensional electronic portal imaging array for exposure to a high dose rate brachytherapy radiation source to obtain a measured response;

a processor for associating the measured response of the imaging array to the high dose rate brachytherapy radiation source to a known dosage;

a processor for determining the high dose rate brachytherapy radiation source position using the method of claim 1;

a calculator for determining a response of the imaging array by calculating an average pixel value for a region of interest of one or more pixels surrounding the determined source position;

a processor for fitting the determined response and/or the known dosage to calculate a dose rate response function for each distance in a set of high dose rate brachytherapy radiation source distances; and a processor for applying the calculated dose rate response function to the high dose rate brachytherapy radiation dosage detected by the imaging array to calibrate the detected high dose rate brachytherapy radiation dosage.

17. A non-transitory computer program product said computer program product comprising:

a computer usable medium and computer readable program code embodied on said computer usable medium for determining a high dose rate brachytherapy source distance from a two dimensional electronic portal imaging array, the computer readable code comprising:

computer readable program code devices (i) configured to cause the computer to expose a two dimensional electronic portal imaging array to a high dose rate brachytherapy radiation source to obtain a measured response;

computer readable program code devices (ii) configured to cause the computer to associate the measured response of the imaging array to the brachytherapy radiation source to a known dosage;

computer readable program code devices (iii) configured to cause the computer to determine the high dose rate brachytherapy radiation source position using the method of claim 1;

computer readable program code devices (iv) configured to cause the computer to determine a response of the imaging array by calculating an average pixel value for a region of interest of one or more pixels surrounding the determined source position;

computer readable program code devices (v) configured to cause the computer to fit the determined response and/or the known dosage to calculate a dose rate response function for each distance in a set of high dose rate brachytherapy radiation source distances; and computer readable program code devices (vi) configured to cause the computer to apply the calculated dose rate response function to the high dose rate brachytherapy radiation dosage detected by the imaging array to calibrate the detected brachytherapy radiation dosage.

18. A method for determining a geometric relationship between a high dose rate brachytherapy radiation source and a brachytherapy implant or a brachytherapy patient, the method including the steps of:

inserting one or more x-ray marker device into the high dose rate brachytherapy implant;

acquiring images of the high dose rate brachytherapy implant using an external x-ray unit and a two dimensional electronic portal imaging array;

calculating the position of the high dose rate brachytherapy implant relative to the imaging array from the acquired images to thereby determine the geometric relationship between the high dose rate brachytherapy radiation source and the high dose rate brachytherapy implant or brachytherapy patient.

19. A system for determining a geometric relationship between a high dose rate brachytherapy radiation source and a high dose rate brachytherapy implant or a high dose rate brachytherapy patient, the system comprising:

a high dose rate brachytherapy implant comprising one or more x-ray marker device;

an external x-ray unit and a two dimensional electronic portal imaging array for acquiring images of the high dose rate brachytherapy implant;

a processor for calculating the position of the high dose rate brachytherapy implant relative to the imaging array from the acquired images to thereby determine the geometric relationship between the high dose rate brachytherapy radiation source and the high dose rate brachytherapy implant or brachytherapy patient.

20. A non-transitory computer program product said computer program product comprising:

a computer usable medium and computer readable program code embodied on said computer usable medium for determining a geometric relationship between a high dose rate brachytherapy radiation source and a high dose rate brachytherapy implant or a high dose rate brachytherapy patient, the computer readable code comprising:

computer readable program code devices (i) configured to cause the computer to acquire images of the high dose rate brachytherapy implant using an external x-ray unit and a two dimensional electronic portal imaging array wherein the high dose rate brachytherapy implant comprises one or more x-ray marker device;

computer readable program code devices (ii) configured to cause the computer to calculate the position of the high dose rate brachytherapy implant relative to the imaging array from the acquired images to thereby determine the geometric relationship between the high dose rate brachytherapy radiation source and the high dose rate brachytherapy implant or high dose rate brachytherapy patient.

\* \* \* \* \*